United States Patent [19]

Attwood et al.

[11] Patent Number: 4,512,924
[45] Date of Patent: Apr. 23, 1985

[54] PYRIDAZO[1,2-A][1,2]DIAZEPINES

[75] Inventors: Michael R. Attwood, Hitchin; Cedric H. Hassall, Harpenden; Robert W. Lambert, Welwyn; Geoffrey Lawton; Sally Redshaw, both of Hitchin, all of England

[73] Assignee: Hoffmann-La Roche Inc., Nutley, N.J.

[21] Appl. No.: 493,876

[22] Filed: May 12, 1983

[30] Foreign Application Priority Data

May 12, 1982 [GB] United Kingdom ............... 8213850
Feb. 28, 1983 [GB] United Kingdom ............... 8305505

[51] Int. Cl.³ .......................................... C07D 487/04
[52] U.S. Cl. ............................... 260/243.3; 260/245.6; 544/61; 544/116; 544/232; 544/235
[58] Field of Search ............... 260/243.3; 544/61, 116

[56] References Cited

U.S. PATENT DOCUMENTS 4,307,094 12/1981 Hassall et al. ............... 544/236
4,341,781 7/1982 Hassall et al. ............... 544/235

FOREIGN PATENT DOCUMENTS 12401 6/1980 European Pat. Off. .
42100 12/1981 European Pat. Off. .

OTHER PUBLICATIONS

Patchett et al., Chem. Abst. 95: 25634j, EP12401.
Hassall et al., Chem. Abst. 96: 199715x, EP42100.

Primary Examiner—Nicholas S. Rizzo
Assistant Examiner—Cecilia Shen
Attorney, Agent, or Firm—John S. Saxe; Bernard S. Leon

[57] ABSTRACT

Novel compounds of the formula

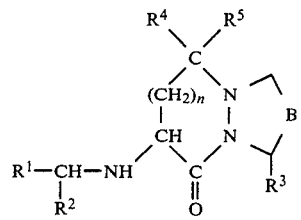

wherein B represents a methylene, ethylene or vinylene group, $R^1$ represents a hydrogen atom or an alkyl, aralkyl, amino-alkyl, mono-alkylamino-alkyl, dialkylamino-alkyl, acylamino-alkyl, phthalimido-alkyl, alkoxycarbonylamino-alkyl, aryloxycarbonylamino-alkyl, aralkoxycarbonylamino-alkyl, alkylaminocarbonylamino-alkyl, arylaminocarbonylamino-alkyl, aralkylaminocarbonylamino-alkyl, alkylsulphonylamino-alkyl or arylsulphonylamino-alkyl group, $R^2$ represents a carboxyl, alkoxycarbonyl or aralkoxycarbonyl group or a group of the formula

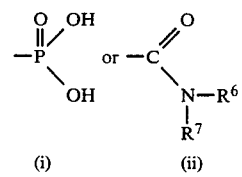

$R^3$ represents a carboxyl, alkoxycarbonyl or aralkoxycarbonyl group, $R^4$ and $R^5$ each represent a hydrogen atom or $R^4$ and $R^5$ together represent an oxo group, $R^6$ and $R^7$ each represent a hydrogen atom or an alkyl or aralkyl group or $R^6$ and $R^7$ together with the nitrogen atom to which they are attached represent a 5-membered or 6-membered heteromonocyclic ring which may contain a further nitrogen atom or an oxygen or sulphur atom, and n stands for zero, 1 or 2, and pharmaceutically acceptable salts thereof have antihypertensive activity and can be used as medicaments in the form of pharmaceutical preparations.

28 Claims, No Drawings

PYRIDAZO[1,2-A][1,2]DIAZEPINES

The present invention relates to bicyclic compounds, a process for the manufacture thereof, medicaments containing said compounds and the use of said compounds.

More particularly, the invention is concerned with bicyclic compounds of the general formula

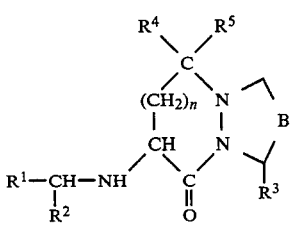

wherein B represents a methylene (—CH$_2$—), ethylene (—CH$_2$—CH$_2$—) or vinylene (—CH=CH—) group, R$^1$ represents a hydrogen atom or an alkyl, aralkyl, amino-alkyl, monoalkylamino-alkyl, dialkylamino-alkyl, acylamino-alkyl, phthalimido-alkyl, alkoxycarbonylamino-alkyl, aryloxycarbonylamino-alkyl, aralkoxycarbonylamino-alkyl, alkylaminocarbonylamino-alkyl, arylaminocarbonylamino-alkyl, aralkylaminocarbonylamino-alkyl, alkylsulphonylamino-alkyl or arylsulphonylamino-alkyl group, R$^2$ represents a carboxyl, alkoxycarbonyl or aralkoxycarbonyl group or a group of the formula

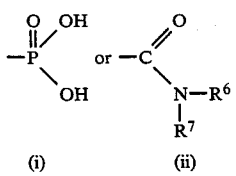

R$^3$ represents a carboxyl, alkoxycarbonyl or aralkoxycarbonyl group, R$^4$ and R$^5$ each represent a hydrogen atom or R$^4$ and R$^5$ together represent an oxo group, R$^6$ and R$^7$ each represent a hydrogen atom or an alkyl or aralkyl group or R$^6$ and R$^7$ together with the nitrogen atom to which they are attached represent a saturated 5 membered or 6-membered heteromonocyclic ring which may contain a further nitrogen atom or an oxygen or sulphur atom, and n stands for zero, 1 or 2, and pharmaceutically acceptable salts thereof.

It will be appreciated that the compounds of formula I contain asymmetric carbon atoms and can therefore exist as optically pure diasteroisomers, as diasteroisomer racemates or as diastereomer mixtures. The present invention is intended to embrace all of these forms. In the compounds of the present invention the configuration at each asymmetric carbon atom is preferably (S).

As used in this Specification, the term "alkyl", alone or in combination, means a straight-chain or branched-chain alkyl group which contains from 1 to 8, preferably from 1 to 4, carbon atoms (e.g. methyl, ethyl, propyl, isopropyl, butyl, tert.butyl, pentyl and hexyl). The aryl group present in an aralkyl, aryloxycarbonylamino-alkyl, aralkoxycarbonylamino-alkyl, arylaminocarbonylamino-alkyl, aralkylaminocarbonylamino-alkyl or arylsulphonylamino-alkyl group is the phenyl group or a phenyl group carrying one or more substituents selected from halogen (i.e. fluorine, chlorine, bromine or iodine), alkyl, alkoxy, trifluoromethyl, phenyl and the like. Examples of aryl groups are phenyl, 4-chlorophenyl, p-tolyl, biphenylyl and the like and examples of aralkyl groups are benzyl, 4-chlorobenzyl, 2-phenylethyl, 3-phenylpropyl, 3-(4-chlorophenyl)propyl, 3-(4-methoxyphenyl)propyl, 4-phenylbutyl and the like. The amino-alkyl group can be, for example, aminomethyl, 2-aminoethyl etc. Methylamino-methyl, 2-methylamino-ethyl, 2-ethylamino-ethyl etc can be mentioned as examples of monoalkylamino-alkyl groups and 2-dimethylamino-ethyl, 2-diethylamino-ethyl, 3-dimethylamino-propyl etc can be mentioned as examples of dialkylamino-alkyl groups. The acyl moiety of an acylamino-alkyl group can be derived from a saturated or unsaturated aliphatic carboxylic acid, from a cycloaliphatic carboxylic acid, from an aromatic carboxylic acid, from an araliphatic carboxylic acid or from a heterocyclic carboxylic acid, examples of such acids being acetic acid, propionic acid, butyric acid, valeric acid, cyclopropane carboxylic acid, cyclopentane carboxylic acid, benzoic acid, p-chlorobenzoic acid, phenylacetic acid, nicotinic acid etc. An alkoxy group and the alkoxy moiety of an alkoxycarbonyl group can be straight-chain or branched-chain and contains from 1 to 8, preferably from 1 to 4, carbon atoms. Specific examples of alkoxycarbonyl groups are methoxycarbonyl and ethoxycarbonyl. The heteromonocyclic ring denoted by R$^6$ and R$^7$ together with the nitrogen atom to which they are attached can be, for example, pyrrolidino, piperidino, morpholino, thiamorpholino and the like.

An interesting sub-class of compounds of formula I comprises those in which R$^1$ represents a hydrogen atom or an alkyl, aralkyl, amino-alkyl, monoalkylamino-alkyl, dialkylamino-alkyl, acylamino-alkyl, alkoxycarbonylamino-alkyl, aryloxycarbonylamino-alkyl, aralkoxycarbonylamino-alkyl, alkylaminocarbonylamino-alkyl, arylaminocarbonylamino-alkyl, aralkylaminocarbonylamino-alkyl, alkylsulphonylamino-alkyl or arylsulphonylamino-alkyl group, R$^2$ represents a carboxyl or alkoxycarbonyl group or a group of formula (i) hereinbefore and R$^3$ represents a carboxyl or alkoxycarbonyl group.

A preferred class of compounds provided by the present invention comprises those in which B represents a methylene or ethylene group. R$^1$ preferably represents an alkyl, aralkyl, acylamino-alkyl, phthalimido-alkyl, aralkoxycarbonylamino-alkyl or aralkylaminocarbonylamino-alkyl group. R$^2$ preferably represents a carboxyl, alkoxycarbonyl or aralkoxycarbonyl group or a group of formula (ii) hereinbefore. Preferably, R$^3$ represents a carboxyl group. Compounds of formula I in which n stands for 2 are also preferred.

From the foregoing it will be evident that particularly preferred compounds of formula I hereinabove are those in which B represents a methylene or ethylene group, R$^1$ represents an alkyl, aralkyl, acylamino-alkyl, phthalimido-alkyl, aralkoxycarbonylamino-alkyl or aralkylaminocarbonylamino-alkyl group, R$^2$ represents a carboxyl, alkoxycarbonyl or aralkoxycarbonylamino group or a group of formula (ii) hereinbefore, R$^3$ represents a carboxyl group and n stands for 2.

Especially preferred compounds of formula I hereinbefore are:

9-(1-Carboxy-3-phenylpropylamino)-octahydro-6,10-dioxo-6H-pyridazo[1,2-a][1,2]diazepine-1-carboxylic acid, 9-(1-ethoxycarbonyl-3-phenylpropylamino)-octahydro-6,10-dioxo-6H-pyridazo[1,2-a][1,2]diazepine-1-carboxylic acid,
8-(1-carboxy-3-phenylpropylamino)-2,3,6,7,8,9-hexahydro-6,9-dioxo-1H,5H-pyrazolo[1,2-a][1,2]diazepine-1-carboxylic acid,
9-(1-benzyloxycarbonyl-3-phenylpropylamino)-octahydro-6,10-dioxo-6H-pyridazo[1,2-a][1,2]diazepine-1-carboxylic acid,
9-(1-carbamoyl-3-phenylpropylamino)-octahydro-6,10-dioxo-6H-pyridazo[1,2-a][1,2]diazepine-1-carboxylic acid,
9-(1-ethylcarbamoyl-3-phenylpropylamino)octahydro-6,10-dioxo-6H-pyridazo[1,2-a][1,2]diazepine-1-carboxylic acid,
9-(1-carboxy-4-phenylbutylamino)-octahydro-6,10-dioxo-6H-pyridazo[1,2-a][1,2]diazepine-1-carboxylic acid,
9-(1-carboxy-2-phenylethylamino)-octahydro-6,10-dioxo-6H-pyridazo[1,2-a][1,2]diazepine-1-carboxylic acid,
9-(1-carboxy-4-methylpentylamino)-octahydro-6,10-dioxo-6H-pyridazo[1,2-a][1,2]diazepine-1-carboxylic acid,
9-(1-ethoxycarbonyl-4-methylpentylamino)-octahydro-6,10-dioxo-6H-pyridazo[1,2-a][1,2]diazepine-1-carboxylic acid,
9-[3-(4-chlorophenyl)-1-ethoxycarbonylpropylamino]-octahydro-6,10-dioxo-6H-pyridazo[1,2-a][1,2]diazepine-1-carboxylic acid,
9-[1-ethoxycarbonyl-3-(4-methoxyphenyl)-propylamino]-octahydro-6,10-dioxo-6H-pyridazo[1,2-a][1,2]diazepine-1-carboxylic acid,
9-[3-(4-biphenylyl)-1-ethoxycarbonylpropylamino]-octahydro-6,10-dioxo-6H-pyridazo[1,2-a][1,2]diazepine-1-carboxylic acid,
9-(1-ethoxycarbonyl-5-phthalimidopentylamino)-octahydro-6,10-dioxo-6H-pyridazo[1,2-a][1,2]diazepine-1-carboxylic acid,
8-(1-ethoxycarbonyl-3-phenylpropylamino)-2,3,6,7,8,9-hexahydro-5,9-dioxo-1H,5H-pyrazolo[1,2-a][1,2]diazepine-1-carboxylic acid,
9-(1-ethoxycarbonyl-3-phenylpropylamino)-octahydro-10-oxo-6H-pyridazo[1,2-a][1,2]diazepine-1-carboxylic acid and
9-(5-benzyloxyformamido-1-ethoxycarbonylpentylamino)-octahydro-6,10-dioxo-6H-pyridazo[1,2-a][1,2]diazepine-1-carboxylic acid.

The following are examples of other interesting compounds of formula I hereinbefore:
8-(1-Ethoxycarbonyl-3-phenylpropylamino)octahydro-6,9-dioxopyridazo[1,2-a]pyridazine-1-carboxylic acid,
tert.butyl 8-(1-ethoxycarbonyl-3-phenylpropylamino)-octahydro-6,9-dioxopyridazo[1,2-a]pyridazine-1-carboxylate,
methyl octahydro-8-(1-methoxycarbonyl-3-phenylpropylamino)-9-oxopyridazo[1,2-a]pyridazine-1-carboxylate,
octahydro-8-(3-phenyl-1-phosphonopropylamino)-6,9-dioxopyridazo[1,2-a]pyridazine-1-carboxylic acid,
8-(1-carboxy-3-phenylpropylamino)-1,4,5,7,8,9-hexahydro-6,9-dioxopyridazo[1,2-a]pyridazine-1-carboxylic acid,
2-(1-carboxy-3-phenylpropylamino)hexahydro-3-oxo-1H-pyrazolo[1,2-a]pyridazine-5-carboxylic acid,
methyl 8-(5-benzyloxyformamido-1-ethoxycarbonylpentylamino)-9-oxopyridazo[1,2-a]pyridazine-1-carboxylate,
8-(5-benzyloxyformamido-1-carboxypentylamino)octahydro-9-oxopyridazo[1,2-a]pyridazine-1-carboxylic acid,
8-(5-amino-1-carboxypentylamino)-octahydro-9-oxopyridazo[1,2-a]pyridazine-1-carboxylic acid
methyl 8-(1-methoxycarbonyl-4-phenylbutylamino)-octahydro-9-oxopyridazo[1,2-a]pyridazine-1-carboxylate,
8-(1-carboxy-4-phenylbutylamino)-octahydro-9-oxopyridazo[1,2-a]pyridazine-1-carboxylic acid,
methyl 8-(1-methoxycarbonyl-4-methylpentylamino)-octahydro-9-oxopyridazo[1,2-a]pyridazine-1-carboxylate,
8-(1-carboxy-4-methylpentylamino)-octahydro-9-oxopyridazo[1,2-a]pyridazine-1-carboxylic acid,
methyl octahydro-8-[1-methoxycarbonyl-5-(3-phenylpropionamido)pentylamino]-9-oxopyridazo[1,2-a]pyridazine-1-carboxylate,
8-[1-carboxy-5-(3-phenylpropionamido)pentylamino]-octahydro-9-oxopyridazo[1,2-a]pyridazine-1-carboxylic acid,
methyl 8-[5-(3-benzylureido-1-ethoxycarbonyl)pentylamino]-octahydro-9-oxopyridazo[1,2-a]pyridazine-1-carboxylate,
8-[5-(3-benzylureido-1-carboxy)pentylamino]-octahydro-9-oxopyridazo[1,2-a]pyridazine-1-carboxylic acid,
methyl octahydro-8-[1-methoxycarbonyl-5-(p-toluenesulphonamido)pentylamino]-9-oxopyridazo[1,2-a]pyridazine-1-carboxylate,
8-[1-carboxy-5-(p-toluenesulphonamido)pentylamino]-octahydro-9-oxopyridazo[1,2-a]pyridazine-1-carboxylic acid,
methyl 8-[[5-(6-benzylformamidohexanamido)-1-ethoxycarbonyl]pentylamino]-octahydro-9-oxopyridazo[1,2-a]pyridazine-1-carboxylate,
8-[[5-(6-benzyloxyformamidohexanamido)-1-carboxy]pentylamino]-octahydro-9-oxopyridazo[1,2-a]pyridazine-1-carboxylic acid and
8-(1-ethoxycarbonyl-3-phenylpropylamino)-1,4,6,7,8,9-hexahydro-6,9-dioxopyridazo[1,2-a]pyridazine-1-carboxylic acid.

Further examples of other interesting compounds of formula I are:
Tert.butyl 9-(1-ethoxycarbonyl-3-phenylpropylamino)-octahydro-6,10-dioxo-6H-pyridazo[1,2-a][1,2]diazepine-1-carboxylate,
tert.butyl 9-(1-benzyloxycarbonyl-3-phenylpropylamino)-octahydro-6,10-dioxo-6H-pyridazo[1,2-a][1,2]diazepine-1-carboxylate,
methyl 9-(1-benzyloxycarbonyl-3-phenylpropylamino)-octahydro-6,10-dioxo-6H-pyridazo[1,2-a][1,2]diazepine-1-carboxylate,
methyl 9-(1-carboxy-3-phenylpropylamino)-octahydro-6,10-dioxo-6H-pyridazo[1,2-a][1,2]diazepine-1-carboxylate,
methyl 9-(1-ethoxycarbonyl-3-phenylpropylamino)-octahydro-6,10-dioxo-6H-pyridazo[1,2-a][1,2]diazepine-1-carboxylate,
ethyl 9-(1-ethoxycarbonyl-3-phenylpropylamino)-octahydro-6,10-dioxo-6H-pyridazo[1,2-a][1,2]diazepine-1-carboxylate,
tert.butyl 9-(1-carbamoyl-3-phenylpropylamino)-octahydro-6,10-dioxo-6H-pyridazo[1,2-a][1,2]diazepine-1-carboxylate, tert.butyl 9-(1-ethylcarbamoyl-3-phenylpropylamino)-octahydro-6,10-dioxo-6H-pyridazo[1,2-a][1,2]diazepine-1-carboxylate, tert.butyl 9-(1-ethoxycarbonyl-4-methylpentylamino)-octahydro-6,10-dioxo-6H-pyridazo[1,2-a][1,2]diazepine-1-carboxylate, tert.butyl 9-[3-(4-chlorophenyl)-1-ethoxycarbonylpropylamino]-octahydro-6,10-dioxo-6H-pyridazo[1,2-a][1,2]diazepine-1-carboxylate, tert.butyl 9-[1-ethoxycarbonyl-3-(4-methoxyphenyl)-propylamino]-octahydro-6,10-dioxo-6H-pyridazo[1,2-a][1,2]diazepine-1-carboxylate, tert.butyl 9-[3-(4-biphenylyl)-1-ethoxycarbonylpropylamino]-octahydro-6,10-dioxo-6H-pyridazo[1,2-a][1,2]diazepine-1-carboxylate, tert.butyl 9-(1-ethoxycarbonyl-5-phthalimidopentylamino)-octahydro-6,10-dioxo-6H-pyridazo[1,2-a][1,2]diazepine-1-carboxylate, tert.butyl 8-(1-ethoxycarbonyl-3-phenylpropylamino)-2,3,6,7,8,9-hexahydro-5,9-dioxo-1H,5H-pyrazolo[1,2-a][1,2]diazepine-1-carboxylate, benzyl 9-(1-ethoxycarbonyl-3-phenylpropylamino)-octahydro-10-oxo-6H-pyridazo[1,2-a][1,2]diazepine-1-carboxylate and tert.butyl 9-(5-benzyloxyformamido-1-ethoxycarbonylpentylamino)-octahydro-6,10-dioxo-6H-pyridazo[1,2-a][1,2]diazepine-1-carboxylate.

According to the process provided by the present invention, the compounds of formula I and their pharmaceutically acceptable salts are manufactured by (a) reacting a compound of the general formula

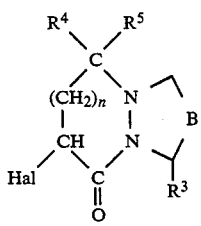

wherein B, $R^3$, $R^4$, $R^5$ and n have the significance given earlier and Hal represents a halogen atom,
with a compound of the general formula

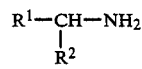

wherein $R^1$ and $R^2$ have the significance given earlier,
or (b) reductively alkylating a compound of the general formula

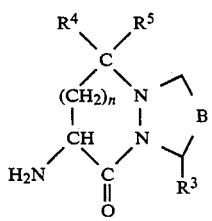

wherein B, $R^3$, $R^4$, $R^5$ and n have the significance given earlier,
with a compound of the general formula

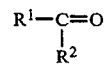

wherein $R^1$ and $R^2$ have the significance given earlier,
or (c) for the manufacture of a compound of formula I in which $R^2$ represents an alkoxycarbonyl or aralkoxycarbonyl group or a group of formula (ii) and $R^3$ represents an alkoxycarbonyl or aralkoxycarbonyl group, reacting a compound of formula IV hereinbefore in which $R^3$ represents an alkoxycarbonyl or aralkoxycarbonyl group with a compound of the general formula

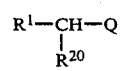

wherein $R^1$ has the significance given earlier, $R^{20}$ represents an alkoxycarbonyl or aralkoxycarbonyl group or a group of formula (ii) and Q represents a leaving atom or group, or (d) for the manufacture of a compound of formula I in which $R^2$ represents a group of formula (ii) and $R^3$ represents a carboxyl group or the tert.butoxycarbonyl group, reacting a compound of formula I in which $R^2$ represents an alkoxycarbonyl group and $R^3$ represents a carboxyl group or the tert.butoxycarbonyl group with a compound of the general formula

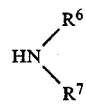

wherein $R^6$ and $R^7$ have the significance given earlier, (e) for the manufacture of a compound of formula I in which B represents an ethylene group, catalytically hydrogenating a compound of formula I in which B represents a vinylene group, or (f) for the manufacture of a compound of formula I in which $R^2$ and/or $R^3$ represents an alkoxycarbonyl or aralkoxycarbonyl group, appropriately esterifying a compound of formula I in which $R^2$ and/or $R^3$ represents a carboxyl group, or (g) for the manufacture of a compound of formula I in which $R^2$ and/or $R^3$ represents a carboxyl group, treating a compound of formula I in which $R^2$ and/or $R^3$ represents an alkoxycarbonyl group with an acid or a base, or (h) for the manufacture of a compound of formula I in which B represents a methylene or ethylene group and $R^2$ and/or $R^3$ represents a carboxyl group subjecting a compound of formula I in which $R^2$ and/or $R^3$ represents an aralkoxycarbonyl group to hydrogenolysis, or (i) for the manufacture of a compound of formula I in which $R^1$ represents an amino-alkyl group, cleaving the alkoxycarbonyl, aryloxycarbonyl or aralkoxycarbonyl group from a corresponding compound of formula I in which $R^1$ represents an alkoxycarbonylamino-alkyl, aryloxycarbonylamino-alkyl or aralkoxycarbonylamino-alkyl group, and (j) if desired, separating a diastereoisomer mixture obtained into the diastereoisomer racemates or optically pure diastereoisomers, and/or (i) if desired, resolving a racemate obtained into the two antipodes, and (l) if desired, converting a compound of formula I into a pharmaceutically acceptable salt.

The reaction of a compound of formula II with a compound of formula III in accordance with embodiment (a) of the process can be carried out in a manner known per se. Conveniently, the reaction is carried out in an inert organic solvent and in the presence of an acid-binding agent. Suitable inert organic solvents include aromatic hydrocarbons (e.g. benzene, toluene etc), dimethylformamide and the like. The acid-binding agent used is preferably an organic base and especially a tertiary organic base such as triethylamine etc. However, an excess of a compound of formula III can be used and can thereby serve as the acid-binding agent. The reaction is conveniently carried out at an elevated temperature (e.g. a temperature of from about 60° C. to the reflux temperature of the reaction mixture).

The reductive alkylation of a compound of formula IV with a compound of formula V in accordance with embodiment (b) of the process can be carried out in a manner known per se. In one method, the reaction can be carried out in the presence of sodium cyanoborohydride in a suitable solvent such as water, a mixture of water and an alkanol (e.g. aqueous ethanol) etc. Conveniently, this reaction is carried out under neutral conditions and at about room temperature. In another method, a compound of formula IV is reacted with a compound of formula V and the Schiff's base formed is catalytically hydrogenated in situ. In this catalytic hydrogenation a vinylene group B is concomitantly reduced to an ethylene group. The catalytic hydrogenation is carried out under the usual conditions; for example, using a noble-metal catalyst (e.g. palladium-on-carbon) or Raney-nickel in an inert organic solvent (e.g. an alkanol such as ethanol) at room temperature and a pressure of 1-10 atmospheres.

The reaction of a compound of formula IV in which $R^3$ represents an alkoxycarbonyl or aralkoxycarbonyl group with a compound of formula VI in accordance with embodiment (c) of the present process is conveniently carried out in the presence of an inert organic solvent (e.g. dimethylformamide, dimethyl sulphoxide, acetonitrile etc) at a temperature of from about 0° C. to 100° C. and in the presence of an acid-binding agent such as an alkali metal carbonate (e.g. sodium carbonate), a tertiary organic base (e.g. triethylamine) or a basic ion-exchange resin. The leaving atom or group denoted by Q in a compound of formula VI can be, for example, a halogen atom such as a bromine atom or a sulphonate group of the formula —O—SO$_2$Y in which Y represents a methyl, trifluoromethyl, p-tolyl or like group.

The reaction of a compound of formula I in which $R^2$ represents an alkoxycarbonyl group and $R^3$ represents a carboxyl group or the tert.butoxycarbonyl group with a compound of formula VII in accordance with embodiment (d) of the present process can be carried out according to methods known per se; for example, in water or in an alcoholic medium at a low temperature (e.g. about 0° C.) or in a sealed tube at an elevated temperature.

The catalytic hydrogenation of a compound of formula I in which B represents a vinylene group in accordance with embodiment (e) of the present process can be carried out in a generally known manner. Suitable catalysts which can be used are noble metal catalysts (e.g. palladium, platinum, ruthenium or rhodium) and Raney-nickel. The noble metal catalyst can be supported on a suitable carrier material (e.g. palladium-on-carbon, rhodium-on-alumina etc). The catalytic hydrogenation can be carried out in a conventional inert organic solvent such as, for example, an aromatic hydrocarbon (e.g. benzene, toluene, xylene etc), an alkanol (e.g. methanol, ethanol etc) or an ether (e.g. dioxane etc). Advantageously, the catalytic hydrogenation is carried out at room temperature and atmospheric pressure, although it can be carried out at an elevated temperature and/or pressure.

The esterification of a compound of formula I in which $R^2$ and/or $R^3$ represents a carboxyl group in accordance with embodiment (f) of the present process can be carried out according to methods known per se. For example, a compound of formula I in which $R^2$ and/or $R^3$ represents a carboxyl group can be reacted with an appropriate alkanol (e.g. methanol, ethanol etc) in the presence of an acid (e.g. a mineral acid such as hydrochloric acid etc) or with a suitable diazoalkane (e.g. diazomethane or phenyldiazomethane). Alternatively, a compound of formula I in which $R^2$ and/or $R^3$ represents a carboxyl group can be converted in a manner known per se (e.g. by treatment with thionyl chloride, phosphorus trichloride or phosphorus pentachloride) into a corresponding acid chloride which is then reacted, likewise in a manner known per se, with an appropriate alkanol. A compound of formula I in which $R^2$ and/or $R^3$ represents a carboxyl group can be reacted with isobutene in the presence of sulphuric acid to give a corresponding compound of formula I in which $R^2$ and/or $R^3$ represents a tert.butoxycarbonyl group.

A compound of formula I in which $R^2$ and/or $R^3$ represents an alkoxycarbonyl group is converted into a corresponding compound of formula I in which $R^2$ and/or $R^3$ represents a carboxyl group in accordance with embodiment (g) of the present process by treatment with an acid or a base. This embodiment of the process is carried out in a manner known per se; for example, by treatment with an alkali metal hydroxide such as sodium hydroxide or potassium hydroxide, conveniently at a temperature between room temperature and the boiling point of the mixture, or, where the alkoxycarbonyl group is the tert.butoxycarbonyl group, by treatment with anhydrous acid.

The hydrogenolysis of a compound of formula I in which $R^2$ and/or $R^3$ represents an aralkoxycarbonyl group to give a compound of formula I in which B represents a methylene or ethylene group and $R^2$ and/or $R^3$ represents a carboxyl group in accordance with embodiment (h) of the present process, can be carried out in a manner known per se. In this hydrogenolysis a vinylene group B is concomitantly reduced to an ethylene group.

The cleavage in accordance with embodiment (i) of the process can be carried out in a manner known per se, with the particular cleavage method chosen depending on the nature of the group to be cleaved off. For example, an aralkoxycarbonyl group (e.g. benzyloxycarbonyl) can be cleaved off by hydrogenolysis or hydrolysis.

The separation of diastereoisomer mixtures into the diastereoisomer racemates or optically pure diastereoisomers in accordance with embodiment (j) of the present process and the resolution of racemates into the two antipodes in accordance with embodiment (k) of the present process can be carried out according to methods known per se.

In accordance with embodiment (l) of the present process, compounds of formula I can be converted into pharmaceutically acceptable salts by treatment with a pharmaceutically acceptable acid or base. Examples of pharmaceutically acceptable acids are inorganic acids such as hydrohalic acids (e.g. hydrobromic acid or hydrochloric acid), sulphuric acid, phosphoric acid and nitric acid, and organic acids such as acetic acid, maleic acid, fumaric acid, tartaric acid, citric acid, methanesulphonic acid and paratoluenesulphonic acid. Examples of pharmaceutically acceptable bases are alkali metal hydroxides (e.g. sodium hydroxide or potassium hydroxide), alkaline earth metal hydroxides (e.g. calcium hydroxide or magnesium hydroxide), ammonium hydroxide and organic bases (e.g. dicyclohexylamine).

The starting materials of formula II used in embodiment (a) of the present process in which B represents an ethylene or vinylene group, $R^3$ represents a carboxyl or alkoxycarbonyl group, $R^4$ and $R^5$ together represent an oxo group and n stands for 1 are generally known compounds. Specific representatives which have not hitherto been described can be prepared as described in the following Examples or in an analogous manner thereto.

The remaining starting materials of formula II are novel and also form an object of the present invention. They can be prepared, for example, by cyclizing a compound of the general formula

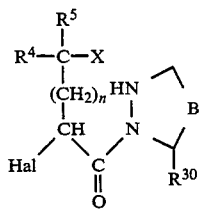
VIII wherein $R^4$, $R^5$, n, B and Hal have the significance given earlier, X represents a halogen atom and $R^{30}$ represents an alkoxycarbonyl group,
and, where necessary, converting the alkoxycarbonyl group $R^{30}$ in the product into a carboxyl group, a different alkoxycarbonyl group or an aralkoxycarbonyl group.

The cyclization of a compound of formula VIII can be carried out in a conventional manner; for example, in the presence of a suitable inert organic solvent (e.g. dimethylformamide or tetrahydrofuran) and optionally in the presence of a base such as an alkali metal carbonate (e.g. sodium carbonate, potassium carbonate etc) or a tertiary organic base (e.g. triethylamine, N-ethylmorpholine etc) at a suitable temperature between 0° C. and 80° C. The cyclization is conveniently carried out in situ; that is to say, without isolating the compound of formula VIII from the medium in which it is prepared.

The conversion of the alkoxycarbonyl group $R^{30}$ in the product, i.e. a compound of formula II in which $R^3$ represents an alkoxycarbonyl group, into a carboxyl group can be carried out in a manner analogous to that described earlier in connection with embodiment (g) of the process of this invention. The thus-obtained compound of formula II in which $R^3$ represents a carboxyl group can then, if desired, be esterified in a manner analogous to that described in embodiment (f) of the present process. Alternatively, a compound of formula II in which $R^3$ represents an alkoxycarbonyl group can be trans-esterified according to known methods to give a compound of formula II in which $R^3$ represents a different alkoxycarbonyl group or an aralkoxycarbonyl group.

The compounds of formula VIII in which $R^4$ and $R^5$ each represent a hydrogen atom can be prepared, for example, by reacting a compound of the general formula

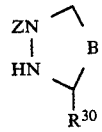
IX with a compound of the general formula

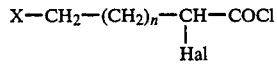
X and removing the benzyloxycarbonyl group from the resulting compound of the general formula

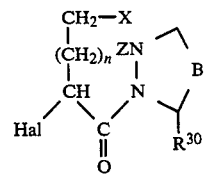
XI in which formulae B, $R^{30}$, n, X and Hal have the significance given earlier and Z represents a benzyloxycarbonyl group.

The reaction of a compound of formula IX, which is a known compound or an analogue of a known compound, with a compound of formula X, which is likewise a known compound or an analogue of a known compound, can be carried out in a generally known manner; for example, in the presence of an inert organic solvent (e.g. a halogenated hydrocarbon such as dichloromethane) and in the presence of an acid-binding agent such as an alkali metal carbonate (e.g. sodium carbonate) or an alkali metal bicarbonate (e.g. sodium bicarbonate) at about room temperature.

The cleavage of the benzyloxycarbonyl group from a compound of formula XI can be carried out, for example, by treatment with hydrogen bromide in glacial acetic acid at about room temperature or using hydrogen in the presence of a catalyst according to known techniques.

The compounds of formula VIII in which $R^4$ and $R^5$ together represent an oxo group can be prepared, for example, by reacting a compound of formula IX hereinbefore with a compound of the general formula

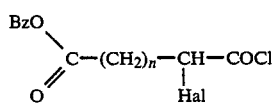
XII wherein n and Hal have the significance given earlier and Bz represents a benzyl group,
removing the benzyl and benzyloxycarbonyl groups from the resulting compound of the general formula

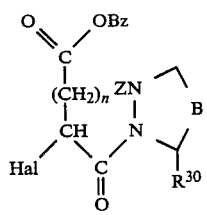

wherein B, $R^{30}$, n, Hal, Bz and Z have the significance given earlier,
and converting the resulting acid of the general formula

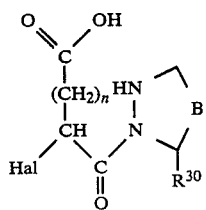

wherein B, $R^{30}$, n and Hal have the significance given earlier,
into a corresponding acid halide.

The reaction of a compound of formula IX with a compound of formula XII, which is a known compound or an analogue of a known compound, can be carried out in a manner analogous to that described earlier in connection with the reaction of a compound of formula IX with a compound of formula X.

The removal of the benzyl and benzyloxycarbonyl groups from a compound of formula XIII can be carried out according to generally known methods; for example, using hydrogen in the presence of a catalyst such as a noble-metal catalyst (e.g. palladium-on-carbon) or, when $R^{30}$ represents other than a tert.butoxycarbonyl group, using hydrogen bromide in glacial acetic acid.

The conversion of an acid of formula XIV into a corresponding acid halide of formula VIII can likewise be carried out according to methods known per se; for example, using an appropriate halogenating agent such as thionyl chloride, phosphorus pentachloride and the like.

The starting materials of formula III used in embodiment (a) of the process are known compounds or analogues of known compounds which can be prepared in a similar manner to the known compounds.

The compounds of formula IV used as starting materials in embodiment (b) of the present process are novel and also form an object of the present invention.

The compounds of formula IV can be prepared, for example, by reacting a compound of formula II with an alkali metal azide and reducing the resulting azide of the general formula

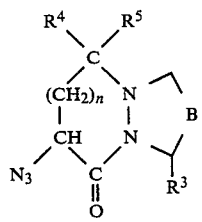

wherein B, $R^3$, $R^4$, $R^5$ and n have the significance given earlier.

The reaction of a compound of formula II with an alkali metal azide, preferably sodium azide, can be carried out in a known manner; for example, in the presence of an inert organic solvent (e.g. a ketone such as acetone) at an elevated temperature (e.g. the reflux temperature of the reaction mixture).

Conventional procedures can be used for the reduction of an azide of formula XV to give a compound of formula IV. A preferred procedure comprises treating an azide of formula XV with triphenylphosphine in a suitable inert organic solvent such as dioxane at about room temperature followed by acid hydrolysis (e.g. using hydrochloric acid).

The compounds of formula IV can also be prepared, for example, by cyclizing a compound of the general formula

XVI wherein B, $R^{30}$, $R^4$, $R^5$, n and X have the significance given earlier and $R^8$ represents a phthaloylamino group, and removing the phthaloyl group from the resulting compound of the general formula

XVII wherein B, $R^{30}$, $R^4$, $R^5$, $R^8$ and n have the significance given earlier;
the alkoxycarbonyl group $R^{30}$ being optionally converted into a carboxyl group, into a different alkoxycarbonyl group or into an aralkoxycarbonyl group before or after the removal of the phthaloyl group as appropriate.

The cyclization of a compound of formula XVI can be carried out in a generally known manner; for example, in substantially the same manner as that described earlier in connection with the cyclization of a compound of formula VIII. The compounds of formula XVI are preferably cyclized in situ.

The removal of the phthaloyl group from a compound of formula XVII can be carried out in a manner known per se using hydrazine, conveniently in an inert organic solvent such as an alkanol (e.g. ethanol) at room temperature or at an elevated temperature (e.g. at the reflux temperature of the mixture).

The optional conversion of an alkoxycarbonyl group $R^{30}$ into a carboxyl group, a different alkoxycarbonyl group or an aralkoxycarbonyl group can be carried out in a manner analogous to that described earlier in connection with the preparation of starting materials of formula II.

The compounds of formula XVI in which $R^4$ and $R^5$ each represent a hydrogen atom can be prepared, for example, by reacting a compound of formula IX hereinbefore with a compound of the general formula

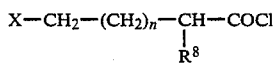  XVIII wherein $R^8$, n and X have the significance given earlier, and removing the benzyloxycarbonyl group from the resulting compound of the general formula

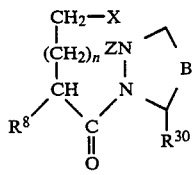  XIX wherein B, $R^{30}$, $R^8$, n, X and Z have the significance given earlier.

The reaction of a compound of formula IX with a compound of formula XVIII, which is a known compund or an analogue of a known compound, can be carried out in the same manner as that described earlier in connection with the reaction of a compound of formula IX with a compound of formula X.

The removal of the benzyloxycarbonyl group from a compound of formula XIX can be carried out in the same manner as that described earlier in connection with the removal of the benzyloxycarbonyl group from a compound of formula XI.

The compounds of formula XVI in which $R^4$ and $R^5$ together represent an oxo group can be prepared, for example, by reacting a compound of formula IX hereinbefore with a compound of the general formula

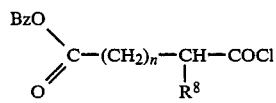  XX wherein $R^8$, n and Bz have the signficance given earlier, removing the benzyl and benzyloxycarbonyl groups from the resulting compound of the general formula

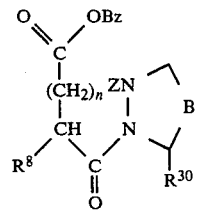  XXI wherein B, $R^8$, $R^{30}$, n, Z and Bz have the significance given earlier, and converting the resulting acid of the general formula

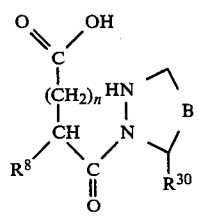  XXII wherein B, $R^8$, $R^{30}$ and n have the significance given earlier, into a corresponding acid halide.

The reaction of a compound of formula IX with a compound of formula XX, which is a known compound or an analogue of a known compound, can be carried out in the same manner as that described earlier in connection with the reaction of a compound of formula IX with a compound of formula X.

The removal of the benzyl and benzyloxycarbonyl groups from a compound of formula XXI can be carried out in the same manner as that described earlier in connection with the removal of these groups from a compound of formula XIII.

The conversion of an acid of formula XXII into a corresponding acid halide of formula XVI can be carried out in an analogous manner to that described earlier in connection with the conversion of an acid of formula XIV into a corresponding acid halide.

The starting materials of formulae V and VI used in embodiments (b) and (c) of the process are known compounds or analogues of known compounds which can be prepared in a similar manner to the known compounds.

The starting materials of formula VII used in embodiment (d) of the process are known compounds.

The compounds of formula I and their pharmaceutically acceptable salts are useful as antihypertensive agents. They inhibit angiotensin converting enzyme (ACE) which brings about the conversion of angiotensin I into angiotensin II and are therefore useful in reducing or alleviating angiotensin-related hypertension.

The activity of the present compounds in inhibiting angiotensin converting enzyme in vitro can be determined by the following test.

The method used is based on the method of Cushman and Cheung (Biochem. Pharmacol., 20. 1637–1648) incorporating the modifications introduced by Hayakari et al (Anal. Biochem., 84. 361–369). The substrate (hippuryl-histidyl-leucine, 2 mM) is incubated with angiotensin converting enzyme in the presence or absence of various concentrations of test substance in potassium phosphate buffer (pH 8.3; 100 mM) containing sodium chloride (300 mM) for 24 minutes at 37° C. (total value 500 μl). (If the test substance is an ester, it is appropriate to cleave it by means of hog liver esterase before carrying out the test). The reaction is terminated by the addition of 3 ml of potassium phosphate buffer (pH 8.3; 200 mM) at 0° C. 2,4,6-Trichloro-s-triazine (3%) in 1.5 ml of dioxane is added and the mixture is agitated until the yellow chromophore has developed fully. The samples are then centrifuged to remove any precipitate which has formed. The yellow chromophore formed by the reaction of the 2,4,6-trichloro-s-triazine with free hippuric acid is measured spectrophotometrically at 382 nm. $IC_{50}$ values are defined as the concentration of test substance which reduces by 50% the cleavage of hippuryl-histidyl-leucine by angiotensin converting enzyme under the aforementioned conditions.

The results obtained in the foregoing test using representative compounds of formula I as the test substance are compiled in the following Table.

Compound A: 9(S)-(1-Carboxy-3-phenyl-propylamino)-octahydro-6,10-dioxo-6H-pyridazo[1,2-a][1,2]diazepine-1(S)-carboxylic acid; isomer A (see Example 1).

Compound B: 8(S)-(1-Carboxy-3-phenyl-propylamino)-octahydro-6,9-dioxopyridazo[1,2-a]pyridazine-1-carboxylic acid; isomer 2 (see Example 4).

Compound C: 8-(1-Carboxy-3-phenylpropylamino)-octahydro-9-oxopyridazo[1,2-a]pyridazine-1-carboxylic acid; racemate B (see Example 9).

Compound D: 9(S)-[1(R and S)-carboxy-4-phenyl-butylamino]-octahydro-6,10-dioxo-6H-pyridazo[1,2-a][1,2]diazepine-1(S)-carboxylic acid (see Example 48).

Compound E: 9(S)-[1(R and S)-carboxy-2-phenyle-thylamino]-octahydro-6,10-dioxo-6H-pyridazo[1,2-a][1,2]diazepine-1(S)-carboxylic acid (see Example 49).

Compound F: 9(S)-[1(R and S)-carboxy-4-methyl-pentylamino]-octahydro-6,10-dioxo-6H-pyridazo[1,2-a][1,2]diazepine-1(S)-carboxylic acid (see Example 50).

TABLE

| Compound | $IC_{50}$ |
|---|---|
| A | $4.2 \times 10^{-9}$ M |
| B | $2.2 \times 10^{-8}$ M |
| C | $5.5 \times 10^{-8}$ M |
| D | $1.1 \times 10^{-8}$ M |
| E | $2.6 \times 10^{-8}$ M |
| F | $1.2 \times 10^{-8}$ M |

The compounds of formula I and their pharmaceutically acceptable salts can be used as medicaments in the form of pharmaceutical preparations which contain them in assocation with a compatible pharmaceutical carrier material. This carrier material can be an organic or inorganic carrier material which is suitable for enteral (e.g. oral) or parenteral administration, examples of such carrier materials being water, gelatin, gum arabic, lactose, starch, magnesium stearate, talc, vegetable oils, polyalkyleneglycols, petroleum jelly etc. The pharmaceutical preparations can be made up in a solid form (e.g. as tablets, dra ees, suppositories or capsules) or in a liquid form (e.g. as solutions, suspensions or emulsions). The pharmaceutical preparations may be subjected to standard pharmaceutical operations such as sterilization and/or may contain adjuvants such as preserving, stabilizing, wetting or emulsifying agents, salts for varying the osmotic pressure or buffers. The pharmaceutical preparations may also contain other therapeutically valuable substances.

The compounds of formula I and their pharmaceutically acceptable salts can be administered to adults in a daily dosage of from about 0.1 mg to 100 mg, preferably about 1 mg to 50 mg, per kilogram body weight. The daily dosage may be administered as a single dose or in divided doses. It will be appreciated that the aforementioned dosage range is given by way of example only and can be varied upwards or downwards depending on factors such as the particular compound or salt being administered, the route of administration, the severity of the indication being treated and the condition of the patient as determined by the attending physician.

The following Examples illustrate the present invention:

EXAMPLE 1

1.25 g of 9(S)-amino-octahydro-6,10-dioxo-6H-pyridazo[1,2-a][1,2]diazepine-1(S)-carboxylic acid monohydrate and 1.8 g of 2-oxo-4-phenylbutyric acid were dissolved in 6 ml of 2N sodium hydroxide solution at room temperature. 0.3 g of sodium cyanoborohydride was added and the mixture was stirred for 50 minutes. A further 0.3 g of sodium cyanoborohydride was then added and, after a further 85 minutes, a further 0.3 g of sodium cyanoborohydride and 0.9 g of 2-oxo-4-phenyl-butyric acid were added. The pH was adjusted to 7.5-8 by the addition of sodium hydroxide solution and the mixture was left to stand for 3 days. 100 ml of diethyl ether, 20 ml of water and 30 g of Duolite C225 ion exchange resin (H+ form) were added and the mixture was stirred well for 100 minutes. The ethereal phase was removed and the aqueous phase containing the resin was poured onto a column charged with a further 10 g of the aforementioned resin. The column was washed with 80 ml of water and then eluted with 200 ml of water containing 2% pyridine. The eluate was evaporated and yielded 1.1 g of crude 9(S)-[1(R and S)-carboxy-3-phenylpropylamino]-octahydro-6,10-dioxo-6H-pyridazo[1,2-a][1,2]diazepine-1(S)-carboxylic acid.

The isomer mixture was separated on columns of Amberlite XAD-2 polystyrene resin using 0.1M aqueous ammonia containing 5% methanol for the elution. Product diastereomer A was eluted before product diastereomer B; diastereomer A also had the higher Rf on silica thin-layer chromatography plates eluted with butan-1-ol/water/acetic acid (4:1:1). There was obtained 0.32 g of diastereomer A and 0.35 g of diastereomer B in the form of ammonium salts, from which ammonia was removed by means of Duolite C225 resin using water containing 2% pyridine for the elution.

The 9(S)-amino-octahydro-6,10-dioxo-6H-pyridazo[1,2-a][1,2]diazepine-1(S)-carboxylic acid monohydrate used as the starting material was prepared as follows:

(A) 16 g of L-glutamic acid γ-benzyl ester and 11 g of phthalic anhydride, both finely powdered, were stirred in 20 ml of toluene at reflux temperature for 2 hours. 50 ml of toluene were added and the mixture was evaporated. A further 80 ml of toluene were then added and the mixture was left to crystallize. Recrystallization from toluene yielded 15 g of α(S)-(2-benzyloxycarbonylethyl)-1,3-dihydro-1,3-dioxo-2-isoindoleacetic acid of melting point 96°-98° C.; $[\alpha]_D^{20} = -50.4°$ (c=1 in methanol).

(B) 56 g of α(S)-(2-benzyloxycarbonylethyl)-1,3-dihydro-1,3-dioxo-2-isoindoleacetic acid in 500 ml of dry diethyl ether were stirred with 40 g of phosphorus pentachloride at room temperature for 2 hours. A further 2 g of phosphorus pentachloride were added, the mixture was stirred for 30 minutes, undissolved solid was filtered off and the filtrate was evaporated. The residue was evaporated twice with toluene, then dissolved in 262 ml of dichloromethane and cooled in ice/water. The mixture was stirred while 262 ml of dichloromethane containing 44 g of tert.butyl 1-(benzyloxycarbonyl)hexahydro-3-pyridazinecarboxylate were added, followed immediately by 420 ml of saturated aqueous sodium bicarbonate. The mixture was stirred overnight at room temperature, then diluted with ethyl acetate and partly evaporated until the emulsion separated. The organic phase was washed with aqueous sodium dihydrogen phosphate, aqueous sodium carbonate and sodium chloride solution, dried and evaporated. The residue was dissolved in 1040 ml of methanol and hydrogenated at atmospheric pressure over 7.4 g of 10% palladium-on-charcoal until uptake of hydrogen ceased. The catalyst was removed and the filtrate was evaporated to give 61 g of crude gamma(S)-(6-tert.butoxycarbonyl-hexahydro-1-pyridazinyl)carbonyl-1,3-dioxo-2-isoindolinebutyric acid (2 diastereomers). Crystallization from ethyl acetate/diethyl ether yielded 19 g of the S,S isomer, melting point 132°–134° C.; $[\alpha]_D^{25} = -54.4°$ (c=0.5 in methanol). Chromatography on silica gel using diethyl ether for the elution yielded the S,R isomer, melting point 134°–137° C. (from ethyl acetate/diethyl ether); $[\alpha]_D^{25} = -6.2°$ (c=0.5 in methanol).

(C) 2.2 g of gamma(S)-(6S-tert.butoxycarbonyl-hexahydro-1-pyridazinyl)carbonyl-1,3-dioxo-2-isoindolinebutyric acid in 60 ml of dry tetrahydrofuran at 0° C. were stirred with 1.1 ml of N-ethylmorpholine and 1.1 g of phosphorus pentachloride. After 1 hour, a further 0.2 ml of N-ethylmorpholine and 0.2 g of phosphorus pentachloride were added and, after a further 5 hours, a further 0.15 ml of N-ethylmorpholine and 0.15 g of phosphorus pentachloride were added. The mixture was left to stand at room temperature overnight, evaporated, the residue was diluted with 150 ml of ethyl acetate, the solution was washed with 1N hydrochloric acid and sodium chloride solution and then dried over magnesium sulphate. Evaporation of the solvent yielded 2.4 g of crude tert.butyl octahydro-6,10-dioxo-9(S)-phthalimido-6H-pyridazo[1,2-a][1,2]diazepine-1(S)-carboxylate. After purification by chromatography on silica gel using diethyl ether for the elution and crystallization from ethyl acetate/diethyl ether the product melted at 182°–185° C.; $[\alpha]_D^{20} = -80.0°$ (c=0.5 in methanol).

(D) 2.4 g of tert.butyl octahydro-6,10-dioxo-9(S)-phthalimido-6H-pyridazo[1,2-a][1,2]diazepine-1(S)-carboxylate were dissolved in 20 ml of trifluoroacetic acid. After 80 minutes, the mixture was evaporated and the residue was re-evaporated twice with toluene. The residue was triturated with ethyl acetate to give 1.7 g of octahydro-6,10-dioxo-9(S)-phthalimido-6H-pyridazo[1,2-a][1,2]diazepine-1(S)-carboxylic acid. A sample recrystallized from acetone/water melted at 307°–310° C. (with decomposition); $[\alpha]_D^{20} = -139°$ (c=0.5 in dimethylformamide).

(E) 4.9 g of octahydro-6,10-dioxo-9(S)-phthalimido-6H-pyridazo[1,2-a][1,2]diazepine-1(S)-carboxylic acid was heated to 70° C. for 40 minutes in 80 ml of ethanol with 1.4 ml of hydrazine hydrate. The mixture was left to stand at room temperature overnight and then evaporated. 100 ml of 2N acetic acid were added, the mixture was stirred at room temperature for 70 minutes and then filtered. The filtrate was evaporated and the residue was re-evaporated with water. The residue was then dissolved in 60 ml of warm water, filtered, the filtrate was concentrated, the residue was diluted with 30 ml of ethanol and left to crystallize. There were obtained 2.65 g of 9(S)-amino-octahydro-6,10-dioxo-6H-pyridazo[1,2-a][1,2]diazepine-1(S)-carboxylic acid monohydrate of melting point 195°–200° C. (with decomposition); $[\alpha]_D^{20} = -174.6°$ (c=0.5 in 2N hydrochloric acid).

EXAMPLE 2

2.3 g of 9(S)-amino-octahydro-6,10-dioxo-6H-pyridazo[1,2-a][1,2]-diazepine-1(S)-carboxylic acid monohydrate were stirred at room temperature in 25 ml of ethanol and 5 ml of water with 1.1 g of ethyl 2-oxo-4-phenylbutyrate and 0.3 g of sodium cyanoborohydride. During the next 48 hours, a further 8 g of ethyl 2-oxo-4-phenylbutyrate and 1.5 g of sodium cyanoborohydride were added in 5 portions to the stirred mixture which was then left to stand for 3 days. The mixture was evaporated, the residue was diluted with 120 ml of ethyl acetate and the solution was extracted with two 50 ml portions of water and with 5 ml of saturated aqueous sodium bicarbonate. The aqueous extract was washed with 30 ml of diethyl ether, then acidified to pH 3–4 and extracted with 100 ml of ethyl acetate and subsequently with 50 ml of ethyl acetate. The combined organic extracts were washed with sodium chloride solution, dried over magnesium sulphate and evaporated. 3.7 g of crude 9(S)-[1(R and S)-ethoxycarbonyl-3-phenylpropylamino]-octahydro-6,10-dioxo-6H-pyridazo[1,2-a][1,2]diazepine-1(S)-carboxylic acid were obtained in the form of a diastereomeric mixture which could be separated on silica thin-layer chromatography plates using diethyl ether containing 10% acetic acid for the elution. Separation of the diastereomers was achieved by chromatography on a silica column using diethyl ether containing 5 to 15% acetic acid for the elution. The diastereomer having the lower Rf (isomer B) was dissolved in toluene and treated with dry hydrogen chloride. The resulting solid was recrystallized from ethanol/ethyl acetate to yield 9(S)-[1(R and S)-ethoxycarbonyl-3-phenylpropylamino]-octahydro-6,10-dioxo-6H-pyridazo[1,2-a][1,2]diazepine-1(S)-carboxylic acid hydrochloride of melting point 202°–207° C. (with decomposition).

EXAMPLE 3

In a manner analogous to that described in the first paragraph of Example 1, from 1.13 g of 8(S)-amino-2,3,6,7,8,9-hexahydro-5,9-dioxo-1H,5H-pyrazolo[1,2-a][1,2]diazepine-1(S)-carboxylic acid and 2.7 g of 2-oxo-4-phenylbutyric acid there were obtained 350 mg of 8(S)-(1-carboxy-3-phenylpropylamino)-2,3,6,7,8,9-hexahydro-5,9-dioxo-1H,5H-pyrazolo[1,2-a][1,2]diazepine-1(S)-carboxylic acid in the form of a lyophilized mixture.

The 8(S)-amino-2,3,6,7,8,9-hexahydro-5,9-dioxo-1H,5H-pyrazolo[1,2-a][1,2]diazepine-1(S)-carboxylic acid used as the starting material was prepared as follows:

(A) 17.2 g of tert.butyl acrylate were treated with a solution of diazomethane in diethyl ether until a yellow colouration persisted for 2 minutes after the addition. The solvent was removed by evaporation, the resulting oil was dissolved in 300 ml of ethanol and the solution obtained was hydrogenated over 10% palladium-oncarbon. The catalyst was removed by filtration and the filtrate was evaporated. The resulting oil was dissolved in 260 ml of ethyl acetate and then a solution of 24 g of sodium bicarbonate in 260 ml of water was added. The stirred mixture was cooled to 0° C. and treated dropwise with a solution of 18.76 g of benzyl chloroformate in 50 ml of ethyl acetate. After 1 hour, the organic layer was separated, washed with 2N hydrochloric acid and sodium chloride solution, dried over magnesium sulphate and evaporated. The resulting oil was chromatographed on silica gel. Elution with ethyl acetate/n-hexane (1:1) yielded 10.81 g (25%) of 1-benzyl 3-tert.butyl 1,3-pyrazolidinedicarboxylate in the form of a white solid of melting point 55°–57° C. (from diethyl ether/n-hexane).

(B) 22.02 g of α(S)-(2-benzyloxycarbonylethyl)-1,3-dihydro-1,3-dioxo-2-isoindoleacetic acid (prepared as described in Example 1) in 210 ml of dry diethyl ether were stirred with 15.01 g of phosphorus pentachloride for 2.5 hours. The mixture was filtered and the filtrate was evaporated. The residue was taken up twice in toluene and evaporated each time, then dissolved in 110 ml of dichloromethane and the solution was cooled to 0° C. The solution was stirred at 0° C. while a solution of 15.3 g of 1-benzyl 3-tert.butyl 1,3-pyrazolidinedicarboxylate in 110 ml of dichloromethane was added. 170 ml of saturated aqueous sodium bicarbonate solution were then added and the mixture was stirred at room temperature for 1 hour. The organic solvent was removed by evaporation and the residue was extracted with ethyl acetate. The extract was washed with sodium chloride solution, dried over magnesium sulphate and evaporated. The oil obtained was chromatographed on silica gel. Elution with ethyl acetate/n-hexane (1:1) yielded 25.62 g (78%) of tert.butyl 1-benzyloxycarbonyl-2-(5-benzyloxycarbonyl-2-phthalimidobutyryl)-3-pyrazolidine-carboxylate (2 diastereomers) in the form of a colourless oil.

(C) 24.97 g of tert.butyl 1-benzyloxycarbonyl-2-(5-benzyloxycarbonyl-2-phthalimidobutyryl)-3-pyrazolidinecarboxylate were dissolved in 250 ml of methanol and hydrogenated over 2 g of 10% palladium-on-carbon. The catalyst was removed by filtration and the filtrate was evaporated to give 16 g (98%) of tert.butyl 2-(5-carboxy-2-phthalimidobutyryl)-3-pyrazolidinecarboxylate (2 diastereomers) in the form of a gum.

(D) A stirred solution of 3.45 g of tert.butyl 2-(5-carboxy-2-phthalimidobutyryl)-3-pyrazolidinecarboxylate and 0.92 g of N-ethylmorpholine in 50 ml of dry tetrahydrofuran was cooled to 0° C. and treated with 1.66 g of phosphorus pentachloride. After 1 hour, a further 0.92 g of N-ethylmorpholine and 1.66 g of phosphorus pentachloride were added and, after a further 1 hour, another 0.92 g of N-ethylmorpholine was added. The solvent was removed by evaporation and the residue was partitioned between water and ethyl acetate. The organic layer was washed with saturated aqueous sodium bicarbonate solution, dried over magnesium sulphate and evaporated. The oil obtained was chromatographed on silica gel. Elution with diethyl ether yielded firstly 1.1 g (33%) of tert.butyl 2,3,6,7,8,9-hexahydro-5,9-dioxo-8(S)-phthalimido-1H,5H-pyrazolo[1,2-α][1,2]diazepine-1(S)-carboxylate in the form of a white foam and then 0.52 g (15%) of tert.butyl 2,3,6,7,8,9-hexahydro-5,9-dioxo-8(S)-phthalimido-1H,5H-pyrazolo[1,2-a][1,2]diazepine-1(R)-carboxylate in the form of a white solid of melting point 180°–181° C. (from ethyl acetate/n-hexane).

(E) In a manner analogous to that described in Example 1(D), from 3.72 g of tert.butyl 2,3,6,7,8,9-hexahydro-5,9-dioxo-8(S)-phthalimido-1H,5H-pyrazolo[1,2-a][1,2]diazepine-(1S)-carboxylate and 30 ml of trifluoroacetic acid there were obtained 2.09 g (65%) of 2,3,6,7,8,9-hexahydro-5,9-dioxo-8(S)-phthalimido-1H,5H-pyrazolo[1,2-a][1,2]diazepine-1(S)-carboxylic acid in the form of a white solid of melting point 232°–233° C. (from acetonitrile).

(F) In a manner analogous to that described in Example 1(E), but carrying out the treatment with hydrazine hydrate at room temperature instead of at 70° C., from 3.57 g of 2,3,6,7,8,9-hexahydro-5,9-dioxo-8(S)-phthalimido-1H,5H-pyrazolo[1,2-a][1,2]diazepine-1(S)-carboxylic acid there were obtained 2.0 g (88%) of 8(S)-amino-2,3,6,7,8,9-hexahydro-5,9-dioxo-1H-5H-pyrazolo[1,2-a][1,2]diazepine-1(S)-carboxylic acid in the form of a lyophilized solid.

EXAMPLE 4

0.9 g of octahydro-8(S)-amino-6,9-dioxopyridazo[1,2-a]pyridazine-1-carboxylic acid (isomer B) and 3.5 g of 2-oxo-4-phenylbutanoic acid were suspended in 25 ml of water and the pH was adjusted to 7 with sodium hydroxide. 0.72 g of sodium cyanoborohydride were added and the solution was stirred at 20° C. for 24 hours. Elution from a sulphonic acid ion exchange resin with 2% pyridine in water followed by evaporation gave 0.8 g of a white solid which was chromatographed on Amberlite XAD 2 using 0.1N ammonium hydroxide in water containing 5% methanol for the elution to give 8(S)-(1-carboxy-3-phenylpropylamino)-octahydro-6,9-dioxopyridazo[1,2-a]pyridazine-1-carboxylic acid as two diastereomers: isomer 1 (240 mg) being eluted first and forming a hydrate from water and isomer 2 (320 mg) being eluted second and forming a hemihydrate from water of melting point 214° C. (decomposition). 200 mg of the amino acid starting material were also obtained from the chromatography.

The octahydro-8(S)-amino-6,9-dioxopyridazo[1,2-a]pyridazine-1-carboxylic acid (isomer B) used as the starting material was prepared as follows:

(A) A solution of 29.5 g of N-phthaloyl-S-aspartic acid β-benzyl ester in 550 ml of dry ether was treated at 0° C. with 16.7 g of phosphorus pentachloride. The mixture was stirred at 0° C. for 1.5 hours and then evaporated. The residual oil was dissolved in 250 ml of dichloromethane and added slowly at 0° C. to a stirred mixture of 26.8 g of 1-benzyloxycarbonylpiperazic acid tert.butyl ester in 500 ml of dichloromethane and 380 ml of saturated aqueous sodium bicarbonate solution. The mixture was stirred at 20° C. for 17 hours and the layers were separated. The organic layer was washed with sodium chloride solution, dried over magnesium sulphate and evaporated. From the residue there were isolated, after column chromatography on silica gel using ethyl acetate/n-hexane (1:2, v/v for the elution), 16.8 g (31%) of oily benzyl tert.butyl hexahydro-2-[3-benzyloxycarbonyl-2(S)-phthalimidopropionyl]-1,3-pyridazinedicarboxylate (diastereomer A) and 21.4 g (39%) of oily benzyl tert.butyl hexahydro-2[3-benzyloxycarbonyl-2(S)-phthalimidopropionyl]-1,3-pyridazinedicarboxylate (diastereomer B).

(B) A solution of 11.1 g of benzyl tert.butyl hexahydro-2-[3-benzyloxycarbonyl-2(S)-phthalimidopropionyl]-1,3-pyridazinedicarboxylate (diastereomer B) in 220 ml of methanol was hydrogenated over 1.1 g of 10% palladium-on-carbon for 18 hours. The catalyst was removed by filtration and the filtrate was evaporated to give 6.9 g (94%) of tert.butyl hexahydro-2-[3-carboxy-2(S)-phthalimidopropionyl]-3-pyridazinecarboxylate (diastereomer B) in the form of a gum.

(C) An ice-cold solution of 6.9 g of tert.butyl hexahydro-2-[3-carboxy-2(S)-phthalimidopropionyl]-3-pyridazinecarboxylate (diastereomer B) in 270 ml of tetrahydrofuran was treated with 3.4 ml of N-ethylmorpholine and 3.4 g of phosphorus pentachloride and the mixture was stirred at 20° C. for 1.5 hours. The solvent was removed in vacuo and the residue was partitioned between ethyl acetate and 0.5N hydrochloric acid. The organic layer was washed successively with sodium chloride solution, saturated sodium bicarbonate solution and sodium chloride solution, and after evaporation yielded 6.6 g (99%) of tert.butyl octahydro-6,9-dioxo-8(S)-phthalimidopyridazo[1,2-a]pyridazine-1-carboxylate (diastereomer B) in the form of white crystals of melting point 131° C. (from ethyl acetate/n-hexane).

(D) 6.6 g of tert.butyl octahydro-6,9-dioxo-8(S)-phthalimidopyridazo[1,2-a]pyradazine-1-carboxylate (diastereomer B) were left to stand for 1 hour at room temperature with 30 ml of trifluoroacetic acid. After evaporation the residue was recrystallized from acetic acid/diethyl ether to give 4.1 g (72%) of octahydro-6,9-dioxo-8(S)-phthalimidopyridazo[1,2-a]pyridazine-1-carboxylic acid (diastereomer B) in the form of white crystals of melting point 275°–277° C. (with decomposition).

(E) A suspension of 7.5 g of octahydro-6,9-dioxo-8(S-phthalimidopyridazo[1,2-a]pyridazine-1-carboxylic acid in 290 ml of ethanol was treated with 3 ml of hydrazine hydrate and the mixture was heated under reflux for 1 hour. The mixture was left to cool and was then filtered. The residue was stirred with 160 ml of 2N acetic acid at 20° C. for 1 hour and the mixture was filtered. The filtrate was evaporated to dryness and the residue was washed with four 10 ml portions of ethanol. There were thus obtained 3.4 g (71%) of octahydro-8(S)-amino-6,9-dioxopyridazo[1,2-a]pyridazine-1-carboxylic acid (diastereomer B) in the form of a white solid of melting point 263°–265° C. (with decomposition).

EXAMPLE 5

A solution of 3.0 g of sodium cyanoborohydride in 40 ml of 50% aqueous ethanol was added to a stirred suspension of 9.3 g of ethyl 2-oxo-4-phenylbutonoate and 3.4 g of octahydro-8(S)-amino-6,9-dioxopyridazo[1,2-a]pyridazine-1-carboxylic acid (diastereomer B) in 90 ml of 50% aqueous ethanol. Two further portions of 3.1 g of ethyl 2-oxo-4-phenylbutanoate were added at 1 hour intervals and the mixture was stirred at 20° C. for 18 hours. Elution from a sulphonic acid ion exchange resin with water containing 2% pyridine and subsequent evaporation gave a white solid which was partitioned between ethyl acetate and water. 1.2 g of unreacted amino acid starting material were recovered from the aqueous layer. 1.8 g of 8(S)-[1-(R,S)-ethoxycarbonyl-3-phenylpropylamino]-octahydro-6,9-dioxopyridazo[1,2-a]pyridazine-1-carboxylic acid were isolated from the organic layer in the form of a white solid of melting point 193°–195° C. (from ethyl acetate), the yield being 45% based on reacted amino acid starting material.

EXAMPLE 6

A solution of 0.6 g of tert.butyl 8(S)-amino-octahydro-6,9-dioxopyridazo[1,2-a]pyridazine-1-carboxylate and 2.4 g of ethyl 2-oxo-4-phenylbutanoate in 30 ml of ethanol was hydrogenated over 0.5 g of 10% palladium-on-carbon in the presence of a molecular sieve for 65 hours. The catalyst was removed by filtration. The filtrate was evaporated and the residue was chromatographed on silica gel to give two diastereomers of tert.butyl 8(S)-(1-ethoxycarbonyl-3-phenylpropylamino)-octahydro-6,9-dioxopyridazo[1,2-a]pyridazine-1-carboxylate; isomer 1 (180 mg) being eluted first and forming white crystals of melting point 122°–123° C. (from ethyl acetate/n-hexane) and isomer 2 (100 mg) being eluted second and forming white crystals of melting point 96°–99° C. (from n-hexane).

The tert.butyl 8(S)-amino-octahydro-6,9-dioxopyridazo[1,2-a]pyridazine-1-carboxylate used as the starting material was prepared as follows:

A solution of 1.0 g of tert.butyl octahydro-6,9-dioxo-8(S)-phthalimidopyridazo[1,2-a]pyridazine-1-carboxylate (diastereomer B) in 50 ml of ethanol was treated with 0.25 ml of hydrazine hydrate and the mixture was left to stand at room temperature for 4 hours. The solvent was removed in vacuo and the residue was stirred with 40 ml of 2N acetic acid for 1 hour. After filtration, the filtrate was made basic with sodium carbonate and extracted with ethyl acetate. From the ethyl acetate extract there was obtained 0.6 g of tert.butyl 8(S)-amino-octahydro-6,9-dioxopyridazo[1,2-a]pyridazine-1-carboxylate (diastereomer B) in the form of an oil.

EXAMPLE 7

1.6 g of methyl 8-bromo-octahydro-9-oxopyridazo[1,2-a]pyridazine-1-carboxylate (racemate A), 1.27 g of methyl 2-amino-4-phenylbutanoate and 0.55 g of triethylamine in 10 ml of dimethylformamide were stirred at 60° C. for 24 hours and then at room temperature for 48 hours. The solvents were removed by evaporation and the residue was partitioned between dichloromethane and saturated aqueous sodium bicarbonate solution. The organic layer was separated, dried over magnesium sulphate and evaporated. The resulting oil was chromatographed on silica gel. Elution with ethyl acetate yielded firstly 0.52 g (23%) of methyl octahydro-8-(1-methoxycarbonyl-3-phenylpropylamino)-9-oxopyridazo[1,2-a]pyridazine-1-carboxylate (racemate A) in the form of a pale yellow oil and subsequently 0.9 g (40%) of methyl octahydro-8-(1-methoxycarbonyl-3-phenylpropylamino)-9-oxopyridazo[1,2-a]pyridazine-1-carboxylate (racemate B) in the form of a pale yellow oil.

The methyl 8-bromo-octahydro-9-oxopyridazo[1,2-a]pyridazine-1-carboxylate (racemate A) used as the starting material was prepared as follows:

(A) A solution of 10 g of 1-benzyloxycarbonylpiperazic acid tert.butyl ester and 16.5 g of 2,4-dibromobutyryl chloride in 50 ml of dichloromethane was stirred at room temperature for 3 hours with 100 ml of saturated aqueous sodium carbonate solution. The organic layer was then separated, washed with saturated aqueous sodium bicarbonate solution and sodium chloride solution, dried over magnesium sulphate and evaporated. The resulting oil was chromatographed on silica gel using diethyl ether for the elution, there being obtained 12.38 g (73%) of 1-benzyl 3-tert.butyl 2-(2,4-dibromobutyryl)-hexahydro-1,3-pyridazinedicarboxylate (2 racemates) in the form of a white solid of melting point 81°–82° C. (from diethyl ether/petroleum ether).

(B) 4 g of 1-benzyl 3-tert.butyl 2-(2,4-dibromobutytyl)-hexahydro-1,3-pyridazinedicarboxylate (2 racemates) were stirred at room temperature for 1 hour with 25 ml of trifluoroacetic acid and the mixture was then evaporated. The resulting oil was dissolved in 20 ml of methanol and esterified using a solution of diazomethane in diethyl ether. Evaporation of the mixture yielded 3.2 g (87%) of 1-benzyl 3-methyl 2-(2,4-dibromobutyryl)-hexahydro-1,3-pyridazinecarboxylate (2 racemates) in the form of a white solid of melting point 76°–76.5° C. (from diethyl ether).

(C) 11 g of 1-benzyl 3-methyl 2-(2,4-dibromobutyryl)-hexahydro-1,3-pyridazinedicarboxylate (2 racemates) were stirred at room temperature for 1 hour with 35 ml of 45% hydrogen bromide solution in glacial acetic acid and the mixture was then evaporated. The resulting oily solid was washed with diethyl ether and then partitioned between dichloromethane and saturated aqueous sodium bicarbonate solution. The organic layer was separated, dried over sodium sulphate and evaporated. The resulting oil was dissolved in 50 ml of dimethylformamide and stirred at 80° C. for 2 hours with 3 g of anhydrous potassium carbonate. The mixture was then evaporated and the residue was partitioned between dichloromethane and saturated aqueous sodium bicarbonate solution. The organic layer was separated, dried over sodium sulphate and evaporated. The residue was chromatographed on silica gel. Elution with tert.butyl methyl ether gave firstly 3.57 g (30%) of methyl 8-bromo-octahydro-9-oxopyridazo[1,2-a]pyridazine-1-carboxylate (racemate A) in the form of a white solid of melting point 95°–96° C. (from ethyl acetate/n-hexane) and subsequently 2.1 g (33%) of methyl 8-bromo-octahydro-9-oxopyridazo[1,2-a]pyridazine-1-carboxylate (racemate B) in the form of a white solid of melting point 102°–103° C. (from ethyl acetate/n-hexane).

EXAMPLE 8

A solution of 160 mg of sodium hydroxide in 8 ml of water was added to a solution of 403 mg of methyl octahydro-8-(1-methoxycarbonyl-3-phenylpropylamino)-9-oxopyridazo[1,2-a]pyridazine-1-carboxylate (racemate A) in 8 ml of methanol and the mixture was stirred at room temperature for 3 hours. The resulting solution was applied to 8 ml of Zerolit 225 ion exchange resin (H+ form). Elution with water containing 2% pyridine yielded 112 mg (30%) of 8-(1-carboxy-3-phenylpropylamino)-octahydro-9-oxopyridazo[1,2-a]pyridazine-1-carboxylic acid (racemate (A) in the form of a white solid which, after crystallization from water, melted at 203°–204° C. (with decomposition).

EXAMPLE 9

A solution of 120 mg of sodium hydroxide in 6 ml of water was added to a solution of 240 mg of methyl octahydro-8-(1-methoxycarbonyl-3-phenylpropylamino)-9-oxopyridazo[1,2-a]pyridazine-1-carboxylate (racemate B) in 6 ml of methanol and the mixture was stirred at room temperature for 3 hours. The resulting solution was applied to 6 ml of Zerolit 225 ion exchange resin (H+ form). Elution with water containing 2% pyridine yielded 173 mg (77%) of 8-(1-carboxy-3-phenylpropylamino)-octahydro-9-oxopyridazo[1,2-a]pyridazine-1-carboxylic acid (racemate B) in the form of a white solid which, after recrystallization from water, melted at 208°–210° C. (with decomposition).

EXAMPLE 10

A solution of about 3.7 g of (3-phenylpropionyl)-phosphonic acid in 100 ml of water was titrated to pH 7 with 15.5 ml of 2N sodium hydroxide. 0.8 g of octahydro-8(S)-amino-6,9-dioxopyridazo[1,2-a]pyridazine-1-carboxylic acid (diastereomer B) was added while stirring and the resulting solution was adjusted to pH 7.5 with 1.5 ml of 2N sodium hydroxide. 0.67 g of sodium cyanoborohydride was added and the mixture was stirred overnight at room temperature. Elution from a sulphonic acid ion-exchange resin with water gave, after evaporation, 0.295 g of octahydro-8(S)-[3-phenyl-1-(R,S)-phosphonopropylamino]-6,9-dioxopyridazo[1,2-a]pyridazine-1(S)-carboxylic acid in the form of a white solid of melting point 165°–185° C. The yield was 40% based on reacted amino acid starting material. Elution of the resin with 2N ammonia gave 0.4 g (50%) of the amino acid starting material.

The (3-phenylpropionyl)-phosphonic acid used as the starting material was prepared as follows:

(A) 10.7 g of trimethylsilyl bromide were added dropwise at room temperature over a period of 1 hour to 8.5 g of dimethyl(3-phenylpropionyl)phosphonate. The mixture was then stirred for a further 1 hour and then evaporated at 30° C./0.1 mm Hg to give 12.5 g of bis(trimethylsilyl)-(3-phenylpropionyl)phosphonate in the form of a pale yellow oil. This oil was used in the next step without further purification.

(B) 6.3 g of bis(trimethylsilyl)-(3-phenylpropionyl)-phosphonate were stirred in 100 ml of water at room temperature for 1 hour. The resulting oily mixture was extracted with two 50 ml portions of diethyl ether and the aqueous layer containing about 3.7 g of (3-phenylpropionyl)-phosphonic acid was used without further purification in the process described in the first paragraph of this Example.

EXAMPLE 11

In a manner analogous to that described in the first paragraph of Example 4, from 90 mg of 8-amino-1,4,6,7,8,9-hexahydro-6,9-dioxopyridazo[1,2-a]pyridazine-1-carboxylic acid there was obtained 8-(1-carboxy-3-phenylpropylamino)-1,4,6,7,8,9-hexahydro-6,9-dioxopyridazo[1,2-a]pyridazine-1-carboxylic acid in the form of a lyophilized mixture of diastereomers.

The 8-amino-1,4,6,7,8,9-hexahydro-6,9-dioxopyridazo[1,2-a]pyridazine-1-carboxylic acid used as the starting material was prepared as follows:

(A) 6.3 ml of tert.butyl hypochlorite were added at −20° C. to a stirred suspension of 10 g of 4-bromo-3,6-dioxo-1,2,3,6-tetrahydropyridazine and 5.83 g of methyl pentadienoate in 150 ml of dichloromethane. The suspension was stirred at −20° C. under nitrogen for 8 hours and then at 20° C. for a further 17 hours. 5.7 g of unreacted 4-bromo-3,6-dioxo-1,2,3,6-tetrahydropyridazine were removed by filtration and the filtrate was evaporated. 2.5 g of methyl 8-bromo-1,4,6,9-tetrahydro-6,9-dioxopyridazo[1,2-a]pyridazine-1-carboxylate were obtained in the form of white crystals of melting point 201°–203° C. (from acetone). Chromatography of the mother liquor on silica gel using ethyl acetate/n-hexane (1:1 v/v) for the elution gave 1.2 g of methyl 7-bromo-1,4,6,9-tetrahydro-6,9-dioxopyridazo[1,2-a]pyridazine-1-carboxylate in the form of white crystals of melting point 137°–141° C. (from toluene).

(B) 2.1 g of methyl 8-bromo-1,4,6,9-tetrahydro-6,9-dioxopyridazo[1,2-a]pyridazine-1-carboxylate and 0.9 g of sodium azide were heated under reflux in 50 ml of acetone for 8 hours. The solvent was removed in vacuo and the residue was partitioned between ethyl acetate and water. From the organic layer there were obtained, after recrystallization from ethyl acetate/n-hexane, 1.06 g of methyl 8-azido-1,4,6,9-tetrahydro-6,9-dioxopyridazo[1,2-a]pyridazine-1-carboxylate of melting point 123°–126° C. (decomposition).

(C) A solution of 1 g of methyl 8-azido-1,4,6,9-tetrahydro-6,9-dioxopyridazo[1,2-a]pyridazine-1-carboxylate and 1 g of triphenylphosphine in 15 ml of dioxane was stirred at 20° C. for 2 hours. After evaporation, the residue was stirred at 20° C. with 40 ml of 2N hydrochloric acid for 1 hours. Triphenylphosphine oxide was removed by filtration and the filtrate was saturated with sodium chloride and extracted into chloroform. From the chloroform extract there was isolated 0.74 g of methyl 8-amino-1,4,6,9-tetrahydro-6,9-dioxopyridazo[1,2-a]pyridazine-1-carboxylate in the form of pale yellow crystals of melting point 193°–194° C. (from ethyl acetate/n-hexane).

(D) 100 mg of methyl 8-amino-1,4,6,9-tetrahydro-6,9-dioxopyridazo[1,2-a]pyridazine-1-carboxylate were dissolved in 4 ml of dry methanol and the pH was adjusted to 4 with hydrogen chloride in methanol. 26 mg of sodium cyanoborohydride were added and the mixture was stirred at 20° C. for 24 hours. A further 26 mg of sodium cyanoborohydride were added and the mixture was stirred for a further 24 hours. Throughout the reaction the pH was maintained at 4 by the occasional addition of hydrogen chloride in methanol. The solution was evaporated to dryness and the residue was partitioned between dilute hydrochloric acid and chloroform, 75 mg of unreacted starting material being obtained from the organic layer. The aqueous layer was made basic with sodium bicarbonate and extracted with chloroform. Evaporation of the chloroform extracts gave 25 mg of methyl 8-amino-1,4,6,7,8,9-hexahydro-6,9-dioxopyridazo[1,2-a]pyridazine-1-carboxylate in the form of white crystals of melting point 174°–175° C. (decomposition) (from ethyl acetate).

(E) 120 mg of methyl 8-amino-1,4,6,7,8,9-hexahydro-6,9-dioxopyridazo[1,2-a]pyridazine-1-carboxylate were stirred with 10 ml of methanol and 0.32 ml of 2N sodium hydroxide solution at 0° C. for 45 minutes. The resulting solution was evaporated. The residue was taken up in water and applied to a column of 10 g of a sulphonic acid ion-exchange resin. The column was washed with water and then elution with 2N ammonium hydroxide gave 100 mg of 8-amino-1,4,6,7,8,9-hexahydro-6,9-dioxopyridazo[1,2-a]pyridazine-1-carboxylic acid in the form of a white lyophilizate.

EXAMPLE 12

0.896 g of 2-amino-hexahydro-3-oxo-1H-pyrazolo[1,2-a]pyridazine-5-carboxylic acid (racemate A) was dissolved in 6 ml of water. 2.4 g of 2-oxo-4-phenylbutyric acid were added and the mixture was adjusted to pH 6 with 2N aqueous sodium hydroxide solution. 0.504 g of sodium cyanoborohydride was then added and the mixture was stirred at room temperature for 22 hours. The resulting solution was applied to 10 g of Zerolit 225 ion-exchange resin (H+ form). Elution with water containing 2% pyridine gave 0.98 g of a crude diastereomeric product. Crystallization from water gave a solid which was recrystallized from methanol to yield 0.36 g (22%) of 2-(1-carboxy-3-phenylpropylamino)-hexahydro-3-oxo-1H-pyrazolo[1,2-a]pyridazine-5-carboxylic acid (racemate A) in the form of a white solid of melting point 233°–235° C. (decomposition).

The remaining crude product was chromatographed on Amberlite XAD-2 polystyrene resin. Elution with 0.1N ammonium hydroxide in water/methanol (95:5, v/v) then gave firstly a further 0.09 g (6%) of the foregoing racemate A and secondly 0.16 g (10%) of 2-(1-carboxy-3-phenylpropylamino)-hexahydro-3-oxo-1H-pyrazolo[1,2-a]pyridazine-5-carboxylic acid (racemate B) which crystallized from aqueous ethanol in the form of a white solid of melting point 200°–202° C. (decomposition).

0.51 g of 2-amino-hexahydro-3-oxo-1H-pyrazolo[1,2-a]pyridazine-5-carboxylic acid (racemate B) was dissolved in 4 ml of water. 1.37 g of 2-oxo-4-phenylbutyric acid were added and the mixture was adjusted to pH 6 using 2N aqueous sodium hydroxide solution. 0.33 g of sodium cyanoborohydride was then added and the mixture was left to stir at room temperature for 22 hours. The product was absorbed on to a strong acidic ion-exchange resin and eluted with water containing 2% pyridine to give 0.62 g of crude product. Crystallization from water gave 0.3 g (32%) of 2-(1-carboxy-3-phenylpropylamino)-hexahydro-3-oxo-1H-pyrazolo[1,2-a]pyridazine-5-carboxylic acid (2 racemates: racemates C and D) in the form of a white solid.

The 2-amino-hexahydro-3-oxo-1H-pyrazolo[1,2-a]pyridazine-5-carboxylic acid (racemates A and B) used as the starting material was prepared as follows:

(A) A solution of 3.2 g of 1-benzyloxycarbonylpiperazic acid tert.butyl ester and 5.01 g of 2,3-dibromopropionyl chloride in 50 ml of dichloromethane was stirred for 1 hour at room temperature with 50 ml of saturated aqueous sodium carbonate solution. The organic layer was then separated, washed with saturated aqueous sodium bicarbonate solution and sodium chloride solution, dried over magnesium sulphate and evaporated. Crystallization from diethyl ether/petroleum ether yielded 3.7 g (69%) of tert.butyl 1-benzyloxycarbonyl-2-(2,3-dibromopropionyl)-hexahydro-3-pyridazinecarboxylate (2 racemates) in the form of a white solid of melting point 105°–106° C.

(B) 1.0 g of tert.butyl 1-benzyloxycarbonyl-2-(2,3-dibromopropionyl)-hexahydro-3-pyridazinecarboxylate (2-racemates) was stirred for 1 hour at room temperature with 15 ml of trifluoroacetic acid and the mixture was then evaporated. The resulting oil was dissolved in 10 ml of ethanol and esterified using a solution of diazomethane in diethyl ether to give 0.89 g (95%) of methyl 1-benzyloxycarbonyl-2-(2,3-dibromopropionyl)-hexahydro-3-pyridazinecarboxylate (2 racemates) in the form of a white solid of melting point 132°–134° C. (from ethanol/diethyl ether).

(C) 5.8 g of methyl 1-benzyloxycarbonyl-2-(2,3-dibromopropionyl)-hexahydro-3-pyridazinecarboxylate (2 racemates) were stirred for 1 hour at room temperature with 15 ml of 45% hydrogen bromide solution in glacial acetic acid and the mixture was then evaporated. The resulting oily solid was washed with diethyl ether and then partitioned between dichloromethane and saturated aqueous sodium bicarbonate solution. The organic phase was separated, dried over sodium sulphate and evaporated. The residue was chromatographed on silica gel. Elution with tert.butyl methyl ether gave firstly 0.4 g (12%) of methyl 2-bromo-hexahydro-3-oxo-1H-pyrazolo[1,2-a]pyridazine-5-carboxylate (racemate A) in the form of a white solid of melting point 115°–117° C. (from ethyl acetate/hexane) and secondly 2.54 g (78%) of methyl 2-bromo-hexahydro-3-oxo-1H-pyrazolo[1,2-a]pyridazine-5-carboxylate (B) in the form of a white solid of melting point 109°–112° C. (from ethyl acetate/n-hexane).

(D) 4.5 g of methyl 2-bromo-hexahydro-3-oxo-1H-pyrazolo[1,2-a]pyridazine-5-carboxylate (2 racemates) and 1.58 g of sodium azide in 30 ml of acetone were stirred and heated under reflux for 48 hours. The mixture was evaporated and the residue was partitioned between dichloromethane and water. The organic phase was separated, dried over magnesium sulphate and evaporated. The residue was chromatographed on silica gel. Elution with diethyl ether/methanol (19:1, v/v) gave firstly 2.5 g (65%) of methyl 2-azido-hexahydro-3-oxo-1H-pyrazolo[1,2-a]pyridazine-5-carboxylate (racemate A) in the form of a white solid of melting point 92°–93° C. (from ethyl acetate/n-hexane) and secondly 1.08 g (28%) of methyl 2-azido-hexahydro-3-oxo-1H-pyrazolo[1,2-a]pyridazine-5-carboxylate (racemate B) in the form of a white solid of melting point 70°–71.5° C. (from diethyl ether/n-hexane).

(E) 1.19 g of methyl 2-azido-hexahydro-3-oxo-1H-pyrazolo[1,2-a]pyridazine-5-carboxylate (racemate A) and 1.31 g of triphenylphosphine in 25 ml of dioxane were stirred at room temperature for 1 hour and the mixture was then evaporated. The residue was treated with 40 ml of 2N aqueous ammonia at 50° C. for 2.5 hours and the precipitated triphenyl phosphine oxide was removed by filtration. Evaporation then yielded 0.756 g (76%) of 2-amino-hexahydro-3-oxo-1H-pyrazolo[1,2-a]pyridazine-5-carboxylic acid (racemate A) in the form of a white solid which, after recrystallization from aqueous methanol, melted at 245°–246° C. (decomposition).

(F) 0.95 g of methyl 2-azido-hexahydro-3-oxo-1H-pyrazolo[1,2-a]pyridazine-5-carboxylate (racemate B) and 1.05 g of triphenylphosphine in 20 ml of dioxane were stirred at room temperature for 1 hour and the mixture was then evaporated. The residue was treated with 40 ml of 2N aqueous ammonia at 50° C. for 2.5 hours and the precipitated triphenyl phosphine oxide was removed by filtration. Evaporation then yielded 0.53 g (66%) of 2-amino-hexahydro-3-oxo-1H-pyrazolo[1,2-a]pyridazine-5-carboxylic acid (racemate B) in the form of a white solid which, after recrystallization from aqueous methanol, melted at 228°–230° C. (decomposition).

EXAMPLE 13

0.873 g of methyl 8-bromo-octahydro-9-oxopyridazo[1,2-a]pyridazine-1-carboxylate (racemate A), 1.016 g of ethyl N$^\epsilon$-benzyloxycarbonyl-L-lysinate and 0.303 g of triethylamine in 5 ml of dimethylformamide were stirred at 60° C. for 16 hours. The solvent was removed by evaporation and the residue was partitioned between dichloromethane and saturated aqueous sodium bicarbonate solution. The organic layer was separated, dried over magnesium sulphate and evaporated. The resulting oil was chromatographed on silica gel. Elution with diethyl ether/methanol (19:1) yielded 0.933 g (60%) of methyl 8-(5-benzyloxyformamido-1-ethoxycarboxylpentylamino)-octahydro-9-oxopyridazo[1,2-a]pyridazine-1-carboxylate (2 diastereomers) in the form of a pale yellow oil.

EXAMPLE 14

A solution of 160 mg of sodium hydroxide in 10 ml of water was added to a solution of 1.04 g of methyl 8-(5-benzyloxyformamido-1-ethoxycarbonylpentylamino)-octahydro-9-oxopyridazo[1,2-a]pyridazine-1-carboxylate (2 diastereomers) in 10 ml of methanol and the mixture was stirred at room temperature for 3 hours. A further 80 mg of sodium hydroxide in 5 ml of water was then added and the mixture was stirred for 2 hours. The resulting solution was applied to 10 ml of Zerolit 225 ion exchange resin (H+ form). Elution with water containing 2% pyridine yielded 600 mg (63%) of 8-(5-benzyloxyformamido-1-carboxypentylamino)-octahydro-9-oxopyridazo[1,2-a]pyridazine-1-carboxylic acid (2 diastereomers) in the form of a white solid (from methanol/acetonitrile).

EXAMPLE 15

250 mg of 8-(5-benzyloxyformamido-1-carboxypentylamino)-octahydro-9-oxopyridazo[1,2-a]pyridazine-1-carboxylic acid (2 diastereomers) in 25 ml of methanol were hydrogenated over 50 mg of 10% palladium-on-carbon for 2.5 hours. The catalyst was removed by filtration and the filtrate was evaporated to give 80 mg (45%) of 8-(5-amino-1-carboxypentylamino)-octahydro-9-oxopyridazo[1,2-a]pyridazine-1-carboxylic acid (2 diastereomers) in the form of a white solid (from acetonitrile).

EXAMPLE 16

2.91 g of methyl 8-bromo-octahydro-9-oxopyridazo[1,2-a]pyridazine-1-carboxylate, 2.48 g of methyl-2-amino-5-phenylpentanoate and 1.01 g of triethylamine in 20 ml of dimethylformamide were stirred at 60° C. for 18 hours. The solvents were removed by evaporation and the residue was partitioned between dichloromethane and saturated aqueous sodium bicarbonate solution. The organic layer was separated, dried over magnesium sulphate and evaporated. Extensive chromatography of the resulting oil on silica gel yielded firstly 0.97 g (23%) of methyl 8-(1-methoxycarbonyl-4-phenylbutylamino)-octahydro-9-oxopyridazo[1,2-a]pyridazine-1-carboxylate (racemate A) in the form of a pale yellow oil and secondly 1.77 g (42%) of methyl 8-(1-methoxycarbonyl-4-phenylbutylamino)-octahydro-9-oxopyridazo[1,2-a]pyridazine-1-carboxylate (racemate B) in the form of a pale yellow oil.

EXAMPLE 17

A solution of 210 mg of sodium hydroxide in 13 ml of water was added to a solution of 740 mg of methyl 8-(1-methoxycarbonyl-4-phenylbutylamino)-octahydro-9-oxopyridazo[1,2-a]pyridazine-1-carboxylate (racemate A) in 13 ml of methanol and the mixture was stirred at room temperature for 13 hours. The resulting solution was applied to 25 ml of Zerolit 225 ion exchange resin (H+ form). Elution with water containing 2% pyridine yielded 0.48 g (69%) of 8-(1-carboxy-4-phenylbutylamino)-octahydro-9-oxopyridazo[1,2-a]pyridazine-1-carboxylic acid (racemate A) in the form of a white solid which, after crystallization from aqueous methanol, melted at 192°–194° C. (with decomposition).

EXAMPLE 13 .

A solution of 240 mg of sodium hydroxide in 15 ml of water was added to a solution of 834 mg of methyl 8-(1-methoxycarbonyl-4-phenylbutylamino)-octahydro-9-oxopyridazo[1,2-a]pyridazine-1-carboxylate (racemate B) in 15 ml of methanol and the mixture was stirred at room temperature for 3 hours. The resulting solution was applied to 30 ml of Zerolit 225 ion exchange resin ($H^+$ form). Elution with water containing 2% pyridine yielded 0.48 g (61%) of 8-(1-carboxy-4-phenylbutylamino)-octahydro-9-oxopyridazo[1,2-a]pyridazine-1-carboxylic acid (racemate B) in the form of a white solid which, after crystallization from aqueous methanol, melted at 213° C. (with decomposition).

EXAMPLE 19

2.04 g of methyl 8-bromo-octahydro-9-oxopyridazo[1,2-a]puridazine-1-carboxylate, 1.23 g of methyl 2-amino-5-methylhexanoate and 0.71 g of triethylamine in 15 ml of dimethylformamide were stirred at 60° C. for 24 hours and then at room temperature for 48 hours. The solvents were removed by evaporation and the residue was partitioned between dichloromethane and saturated aqueous sodium bicarbonate solution. The organic layer was separated, dried over magnesium sulphate and evaporated. Extensive chromatography of the resulting oil on silica gel gave firstly 0.35 g (14%) of methyl 8-(1-methoxycarbonyl-4-methylpentylamino)-octahydro-9-oxopyridazo[1,2-a]pyridazine-1-carboxylate (racemate A) in the form of a white solid of melting point 81°–84° C. (from ethyl acetate/n-hexane) and secondly 0.15 g (6%) of methyl 8-(1-methoxycarbonyl-4-methylpentylamino)-octahydro-9-oxopyridazo[1,2-a]pyridazine-1-carboxylate (racemate B) in the form of a pale yellow oil.

EXAMPLE 20

A solution of 156 mg of sodium hydroxide in 8 ml of water was added to a solution of 490 mg of methyl 8-(1-methoxycarbonyl-4-methylpentylamino)-octahydro-9-oxopyridazo[1,2-a]pyridazine-1-carboxylate (racemate A) in 8 ml of methanol and the mixture was stirred at room temperature for 3 hours. The resulting solution was applied to 20 ml of Zerolit 225 ion exchange resin ($H^+$ form). Elution with water containing 2% pyridine yielded 210 mg (47%) of 8-(1-carboxy-4-methylpentylamino)-octahydro-9-oxopyridazo[1,2-a]pyridazine-1-carboxylic acid (racemate A) in the form of a white solid which, after crystallization from water/acetonitrile, melted at 181°–184° C. (with decomposition).

EXAMPLE 21

A solution of 48 mg of sodium hydroxide in 3 ml of water was added to a solution of 150 mg of methyl 8-(1-methoxycarbonyl-4-methylpentylamino)-octahydro-9-oxopyridazo[1,2-a]pyridazine-1-carboxylate (racemate B) in 3 ml of methanol and the mixture was stirred at room temperature for 2.5 hours. The resulting solution was applied to 8 ml of Zerolit 225 ion exchange resin ($H^+$ form). Elution with water containing 2% pyridine yielded 66 mg (48%) of 8-(1-carboxy-4-methylpentylamino)-octahydro-9-oxopyridazo[1,2-a]pyridazine-1-carboxylic acid (racemate B) in the form of a white solid which, after crystallization from water/acetonitrile, melted at 190°–191° C. (with decomposition).

EXAMPLE 22

2.91 g of methyl 8-bromo-octahydro-9-oxopyridazo[1,2-a]pyridazine-1-carboxylate, 3.5 g of methyl $N^6$-(3-phenylpropionyl)-L-lysinate and 1.01 g of triethylamine in 10 ml of dimethylformamide were stirred at 60° C. for 18 hours. The solvents were removed by evaporation and the residue was partitioned between dichloromethane and saturated aqueous sodium bicarbonate solution. The organic layer was separated, dried over magnesium sulphate and evaporated. The resulting oil was chromatographed on silica gel. Elution with diethyl ether/methanol (19:1) yielded 2.6 g (52%) of methyl octahydro-8-[1-methoxycarbonyl-5-(3-phenylpropionamido)pentylamino]-9-oxopyridazo[1,2-a]pyridazine-1-carboxylate (2 diastereomers) in the form of a pale yellow oil.

EXAMPLE 23

A solution of 480 mg of sodium hydroxide in 20 ml of water was added to a solution of 2.08 g of methyl octahydro-8-[1-methoxycarbonyl-5-(3-phenylpropionamido)pentylamino]-9-oxopyridazo[1,2-a]pyridazine-1-carboxylate (2 diastereomers) in 20 ml of methanol and the mixture was stirred at room temperature for 3 hours. The resulting solution was applied to 40 ml of Zerolit 225 ion exchange resin ($H^+$ form). Elution with water containing 2% pyridine yielded 920 mg (48%) of 8-[1-carboxy-5-(3-phenylpropionamido)pentylamino]-octahydro-9-oxopyridazo[1,2-a]pyridazine-1-carboxylic acid (2 diastereomers) in the form of a white solid (from water/acetonitrile).

EXAMPLE 24

1.75 g of methyl 8-bromo-octahydro-9-oxopyridazo[1,2-a]pyridazine-1-carboxylate, 2.46 g of ethyl $N^6$-benzylcarbamoyl-L-lysinate and 0.61 g of triethylamine in 10 ml of dimethylformamide were stirred at 60° C. for 24 hours and then at room temperature for 16 hours. The solvents were removed by evaporation and the residue was partitioned between dichloromethane and saturated aqueous sodium bicarbonate solution. The organic layer was separated, dried over magnesium sulphate and evaporated. The resulting oil was chromatographed on silica gel. Elution with dichloromethane/methanol (9:1) yielded 1.14 g (37%) of methyl 8-[5-(3-benzylureido-1-ethoxycarbonyl)pentylamino]-octahydro-9-oxopyridazo[1,2-a]pyridazine-1-carboxylate (2 diastereomers) in the form of a pale yellow oil.

EXAMPLE 25

A solution of 80 mg of sodium hydroxide in 10 ml of water was added to a solution of 775 mg of methyl 8-[5-(3-benzylureido-1-ethoxycarbonyl)pentylamino]octahydro-9-oxopyridazo[1,2-a]pyridazine-1-carboxylate (2 diastereomers) in 10 ml of methanol and the mixture was stirred at room temperature for 2 hours. A further 40 mg of sodium hydroxide in 5 ml of water was then added and the mixture was stirred for 2 hours. The resulting solution was applied to 30 ml of Zerolit 225 ion exchange resin ($H^+$ form). Elution with water containing 2% pyridine yielded 370 mg (52%) of 8-[5-(3-benzylureido-1-carboxy)pentylamino]-octahydro-9-oxopyridazo[1,2-a]pyridazine-1-carboxylic acid in the form of a lyophilized mixture of diastereomers.

EXAMPLE 26

2.91 g of methyl 8-bromo-octahydro-9-oxopyridazo[1,2-a]pyridazine-1-carboxylate, 3.77 g of methyl $N^2$-tolylsulphonyl-L-lysinate and 1.01 g of triethylamine in 20 ml of dimethylformamide were stirred at 60° for 18 hours. The solvents were removed by evaporation and the residue was partitioned between dichloromethane and saturated aqueous sodium bicarbonate solution. The organic layer was separated, dried over magnesium sulphate and evaporated. The resulting oil was chromatographed on silica gel. Elution with diethyl ether/methanol (19:1) yielded 3.63 g (69%) of methyl octahydro-8-[1-methoxycarbonyl-5-(p-toluenesulphonamido)pentylamino]-9-oxopyridazo[1,2-a]pyridazine-1-carboxylate (2 diastereomers) in the form of a pale yellow oil.

EXAMPLE 27

A solution of 160 mg of sodium hydroxide in 10 ml of water was added to a solution of 1.05 g of methyl octahydro-8-[1-methoxycarbonyl-5-(p-toluenesulphonamido)pentylamino]-9-oxopyridazo[1,2-a]pyridazine-1-carboxylate (2 diastereomers) in 15 ml of methanol and the mixture was stirred at room temperature for 2.5 hours. A further 80 mg of sodium hydroxide in 5 ml of water was then added and the mixture was stirred for 1 hour. The resulting solution was applied to 40 ml of Zerolit 225 ion exchange resin (H+ form). Elution with water containing 2% pyridine yielded 552 mg (56%) of 8-[1-carboxy-5-(p-toluenesulphonamido)pentylamino]-octahydro-9-oxopyridazo[1,2-a]pyridazine-1-carboxylic acid (2 diastereomers) in the form of a white solid.

EXAMPLE 28

1.05 g of methyl 8-bromo-octahydro-9-oxopyridazo[1,2-a]pyridazine-1-carboxylate, 1.81 g of ethyl N6-(6-benzyloxyformamidohexanoyl)-L-lysinate and 0.61 g of triethylamine in 8 ml of dimethylformamide were stirred at 70° C. for 18 hours. The solvents were removed by evaporation and the residue was partitioned between dichloromethane and saturated aqueous sodium bicarbonate solution. The organic layer was separated, dried over magnesium sulphate and evaporated. The resulting oil was chromatographed on silica gel. Elution with dichloromethane/methanol (9:1) yielded 1.21 g (53%) of methyl 8-[[5-(6-benzyloxyformamidohexanamido)-1-ethoxycarbonyl]pentylamino]-octahydro-9-oxopyridazo[1,2-a]pyridazine-1-carboxylate (2 diastereomers) in the form of a pale yellow oil.

EXAMPLE 29

A solution of 115 mg of sodium hydroxide in 8 ml of water was added to a solution of 900 mg of methyl 8-[[5-(6-benzyloxyformamidohexanamido)-1-ethoxycarbonyl]pentylamino]-octahydro-9-oxopyridazo[1,2-a]pyridazine-1-carboxylate (2 diastereomers) in 12 ml of methanol and the mixture was stirred at room temperature for 2.5 hours. A further 57 mg of sodium hydroxide in 4 ml of water was then added and the mixture was stirred for 2.5 hours. The resulting solution was applied to 30 ml of Zerolit 225 ion exchange resin (H+ form). Elution with water containing 2% pyridine yielded 320 mg (38%) of 8-[[5-(6-benzyloxyformamidohexanamido)-1-carboxy]pentylamino]-octahydro-9-oxopyridazo[1,2-a]pyridazine-1-carboxylic acid (2 diastereomers) in the form of a white solid.

EXAMPLE 30

In a manner analogous to that described in Example 5, from 1.78 g of 8-amino-1,4,6,7,8,9-hexahydro-6,9-dioxopyridazo[1,2-a]pyridazine-1-carboxylic acid there was obtained in 30% yield (based on reacted amino acid starting material) 0.54 g of 8(S)-[1-(R,S)-ethoxycarbonyl-3-phenylpropylamino-1,4,6,7,8,9-hexahydro-6,9-dioxopyridazo[1,2-a]pyridazine-1-carboxylic acid in the form of an oil. The diastereomers were separated by chromatography on silica gel (elution with 5% acetic acid in diethyl ether) to give two solids of melting point 166°–167° C. and 183°–184° C. (from ethyl acetate/n-hexane).

EXAMPLE 31

5.94 g of tert.butyl 9(S)-amino-octahydro-6,10-dioxo-6H-pyridazo[1,2-a][1,2]diazepine-1(S)-carboxylate, 5.42 g of ethyl 2-bromo-4-phenylbutanoate and 2.0 g of triethylamine were dissolved in 65 ml of acetonitrile and the solution was boiled under reflux for 17 hours. After evaporation, the residue was partitioned between ethyl acetate and water. The organic layer was washed successively with 2N aqueous acetic acid and aqueous sodium carbonate solution and then evaporated. From the residue there were isolated, after column chromatography on silica gel using diethyl ether/n-hexane for the elution, 3.1 g of tert.butyl 9(S)-[1(R)-ethoxycarbonyl-3-phenylpropylamino]-octahydro-6,10-dioxo-6H-pyridazo[1,2-a][1,2]diazepine-1(S)-carboxylate in the form of a gum and 3.25 g of tert.butyl 9(S)-[1(S)-ethoxycarbonyl-3-phenylpropylamino]-octahydro-6,10-dioxo-6H-pyridazo[1,2-a][1,2]diazepine-1(S)-carboxylate in the form of white crystals of melting point 55°–58° C. after treatment with hexane.

The tert.butyl 9(S)-amino-octahydro-6,10-dioxo-6H-pyridazo[1,2-a][1,2]diazepine-1(S)-carboxylate used as the starting material was prepared as follows:

8.54 g of tert.butyl octahydro-6,10-dioxo-9(S)-phthalimido-6H-pyridazo[1,2-a][1,2]diazepine-1(S)-carboxylate were suspended in 85 ml of ethanol and 2 ml of hydrazine hydrate were added. The mixture was stirred at 20° C. for 2.5 hours and then evaporated. The residue was stirred at 20° C. for 1 hour with 2N aqueous acetic acid and then filtered. The filtrate was made basic with solid sodium carbonate and extracted with dichloromethane. The organic extract was dried and evaporated to give 5.9 g of tert.butyl 9(S)-amino-octahydro-6,10-dioxo-6H-pyridazo[1,2-a][1,2]diazepine-1(S)-carboxylate in the form of a gum.

EXAMPLE 32

131.8 g of tert.butyl 9(S)-amino-octahydro-6,10-dioxo-6H-pyridazo[1,2-a][1,2]diazepine-1(S)-carboxylate and 61.6 ml of triethylamine were dissolved in 2.8 l of acetonitrile. The solution was treated with 150.9 g of ethyl 2(R)-trifluoromethanesulphonyloxy-4-phenylbutanoate [prepared by standard procedures from 2(R)-hydroxy-4-phenylbutanoic acid] and the mixture was stirred at 20° C. for 90 minutes. The solution was evaporated and the residual oil was partitioned between ethyl acetate and water. The organic layer was dried and evaporated and the residue was filtered through a short column of silica gel using ethyl acetate/n-hexane (3:1) for the elution. Evaporation of the eluate gave 187.5 g of tert.butyl 9(S)-[1(S)-ethoxycarbonyl-3-phenylpropylamino]-octahydro-6,10-dioxo-6H-pyridazo[1,2-a][1,2]diazepine-1(S)-carboxylate.

EXAMPLE 33

13.7 g of tert.butyl 9(S)-amino-octahydro-6,10-dioxo-6H-pyridazo[1,2-a][1,2]diazepine-1(S)-carboxylate and 29 g of ethyl 2-oxo-4-phenylbutanoate were stirred at 20° C. for 17 hours in 200 ml of tetrahydrofuran in the presence of 15 g of powdered 4A molecular sieve. Five 1.5 g portions of sodium cyanoborohydride were added at hourly intervals and the stirring was continued for a further 2 hours. Solvent was removed by evaporation and the residue was partitioned between ethyl acetate and aqueous sodium carbonate solution. The organic layer was evaporated and the residue was chromatographed on silica gel using diethyl ether/n-hexane for the elution, there being obtained 4.8 g of tert.butyl 9(S)-[1(R)-ethoxycarbonyl-3-phenylpropylamino]-octahydro-6,10-dioxo-6H-pyridazo[1,2-a][1,2]diazepine-1(S)-carboxylate and 4.1 g of tert.butyl 9(S)-[1(S)ethoxycarbonyl-3-phenylpropylamino]-octahydro-6,10-dioxo-6H-pyridazo[1,2-a][1,2]diazepine-1(S)-carboxylate.

EXAMPLE 34

2.0 g of tert.butyl 9(S)-amino-octahydro-6,10-dioxo-6H-pyridazo[1,2-a][1,2]diazepine-1(S)-carboxylate and 4.2 g of ethyl 2-oxo-4-phenylbutanoate were dissolved in 50 ml of ethanol containing 5 ml of acetic acid. 4 g of powdered molecular sieve were added and the mixture was hydrogenated over 10% palladium-on-carbon at 20° C. and 4 atmospheres for 40 hours. Filtration followed by evaporation gave an oily residue which was chromatographed on silica gel using ethyl acetate/n-hexane for the elution. There were obtained 950 mg of tert.butyl 9(S)-[1(R)-ethoxycarbonyl-3-phenylpropylamino]-octahydro-6,10-dioxo-6H-pyridazo[1,2-a][1,2]diazepine-1(S)-carboxylate and 870 mg of tert.butyl 9(S)-[1(S)-ethoxycarbonyl-3-phenylpropylamino]-octahydro-6,10-dioxo-6H-pyridazo[1,2-a][1,2]diazepine-1(S)-carboxylate.

EXAMPLE 35

860 mg of tert.butyl 9(S)-[1(S)-ethoxycarbonyl-3-phenylpropylamino]-octahydro-6,10-dioxo-6H-pyridazo[1,2-a][1,2]diazepine-1(S)-carboxylate were dissolved in 1 ml of acetic acid and the solution was treated with 4 ml of 45% hydrogen bromide in acetic acid. The solution was left to stand at 20° C. for 1 hour and was then evaporated. The residue was stirred with diethyl ether and filtered to give 840 mg of 9(S)-[1(S)-ethoxycarbonyl-3-phenylpropylamino]-octahydro-6,10-dioxo-6H-pyridazo[1,2-a][1,2]diazepine-1(S)-carboxylic acid hydrobromide of melting point 216°–218° C. (from ethanol/ethyl acetate).

EXAMPLE 36

In a manner analogous to that described in Example 35, from 5.4 of tert.butyl 9(S)-[1(R)-ethoxycarbonyl-3-phenylpropylamino]-octahydro-6,10-dioxo-6H-pyridazo[1,2-a][1,2]diazepine-1(S)-carboxylate there were obtained 4.41 g of 9(S)-[1(R)-ethoxycarbonyl-3-phenylpropylamino]octahydro-6,10-dioxo-6H-pyridazo[1,2-a][1,2]diazepine-1(S)-carboxylic acid hydrobromide of melting point 201°–203° C. (from ethanol/ethyl acetate).

EXAMPLE 37

In a manner analogous to that described in Example 34, from 5.34 g of 2-oxo-4-phenylbutanoic acid and 2.97 g of tert.butyl 9(S)-amino-octahydro-6,10-dioxo-6H-pyridazo[1,2-a][1,2]diazepine-1(S)-carboxylate there were obtained 1.7 g of tert.butyl 9(S)-[1(R)-carboxy-3-phenylpropylamino]-octahydro-6,10-dioxo-6H-pyridazo[1,2-a][1,2]diazepine-1(S)-carboxylate and 1.75 g of tert.butyl 9(S)-[1(S)-carboxy-3-phenylpropylamino]-octahydro-6,10-dioxo-6H-pyridazo[1,2-a][1,2]diazepine-1(S)-carboxylate, both diastereomers being isolated in the form of gums after chromatography on silica gel.

EXAMPLE 38

500 mg of tert.butyl 9(S)-[1(S)-carboxy-3-phenylpropylamino]-octahydro-6,10-dioxo-6H-pyridazo[1,2-a][1,2]diazepine-1(S)-carboxylate were dissolved in diethyl ether and treated at 20° C. with a solution of phenyldiazomethane in diethyl ether. The solution was washed with aqueous sodium bicarbonate solution, dried and evaporated. The residue was chromatographed on silica gel using ethyl acetate/n-hexane (1:1) for the elution to give 430 mg of tert.butyl 9(S)-[1(S)-benzyloxycarbonyl-3-phenylpropylamino]-octahydro-6,10-dioxo-6H-pyridazo[1,2-a][1,2]diazepine-1(S)-carboxylate in the form of a gum.

EXAMPLE 39

410 mg of tert.butyl 9(S)-[1(S)-benzyloxycarbonyl-3-phenylpropylamino]-octahydro-6,10-dioxo-6H-pyridazo[1,2-a][1,2]diazepine-1(S)-carboxylate were treated with 3 ml of trifluoroacetic acid, the solution was left to stand at 20° C. for 1.5 hours and then evaporated. The residual foam was taken up in ethyl acetate and a solution of hydrogen chloride in ethyl acetate was added. The precipitated solid was filtered off, there being obtained 330 mg of 9(S)-[1(S)-benzyloxycarbonyl-3-phenylpropylamino]-octahydro-6,10-dioxo-6H-pyridazo[1,2-a][1,2]diazepine-1(S)-carboxylic acid hydrochloride in the form of a white solid of melting point 198°–202° C.

EXAMPLE 40

260 mg of 9(S)-[1(S)-benzyloxycarbonyl-3-phenylpropylamino]-octahydro-6,10-dioxo-6H-pyridazo[1,2-a][1,2]diazepine-1(S)-carboxylic acid were dissolved in diethyl ether and the solution was treated at 20° C. with a solution of diazomethane in diethyl ether. After 10 minutes, the solution was washed with aqueous sodium bicarbonate solution, dried and evaporated. Chromatography of the residual gum on silica gel using ethyl acetate/hexane (1:1) for the elution gave 180 mg of methyl 9(S)-[1(S)-benzyloxycarbonyl-3-phenylpropylamino]-octahydro-6,10-dioxo-6H-pyridazo[1,2-a][1,2]diazepine-1(S)-carboxylate in the form of a colourless gum.

EXAMPLE 41

170 mg of methyl 9(S)-[1(S)-benzyloxycarbonyl-3-phenylpropylamino]-octahydro-6,10-dioxo-6H-pyridazo[1,2-a][1,2]diazepine-1(S)-carboxylate were dissolved in 5 ml of acetic acid and hydrogenated over 10% palladium-on-carbon at 20° C. and under atmospheric pressure for 17 hours. The catalyst was removed by filtration and the filtrate was evaporated. The residue was taken up in ethyl acetate and a solution of hydrogen chloride in ethyl acetate was added. The precipitated solid was filtered off to give 85 mg of methyl 9(S)-[1(S)-carboxy-3-phenylpropylamino]-octahydro-6,10-dioxo-6H-pyridazo[1,2-a][1,2]diazepine-1(S)-carboxylate in the form of a white solid having a diffuse melting point.

EXAMPLE 42

715 mg of 9(S)-[1(R and S)-ethoxycarbonyl-3-phenylpropylamino]-octahydro-6,10-dioxo-6H-pyridazo[1,2-a][1,2]diazepine-1(S)-carboxylic acid were dissolved in diethyl ether and the solution was treated with a solution of diazomethane in diethyl ether. The diastereomers were separated by chromatography on silica gel using ethyl acetate/n-hexane (1:1) for the elution and were isolated in the form of their crystalline hydrochloride salts from ethyl acetate, there being obtained methyl 9(S)-[1(R)-ethoxycarbonyl-3-phenylpropylamino]-octahydro-6,10-dioxo-6H-pyridazo[1,2-a][1,2]diazepine-1(S)-carboxylate hydrochloride of melting point 161°–163° C. (decomposition) and methyl 9(S)-[1(S)-ethoxycarbonyl-3-phenylpropylamino]-octahydro-6,10-dioxo-6H-pyridazo[1,2-a][1,2]diazepine-1(S)-carboxylate hydrochloride of melting point 175°–178° C. (decomposition).

EXAMPLE 43

500 mg of 9(S)-[1(S)-ethoxycarbonyl-3-phenylpropylamino]-octahydro-6,10-dioxo-6H-pyridazo[1,2-a][1,2]diazepine-1(S)-carboxylic acid were dissolved in 30 ml of ethanol and the solution was saturated with dry hydrogen chloride. After standing at 20° C. for 17 hours, the solution was evaporated and the residue was treated with diethyl ether. Filtration gave ethyl 9(S)-[1(S)-ethoxycarbonyl-3-phenylpropylamino]-octahydro-6,10-dioxo-6H-pyridazo[1,2-a][1,2]diazepine-1(S)-carboxylate hydrochloride in the form of a white solid of melting point 187°–189° C. (decomposition).

EXAMPLE 44

487 mg of tert.butyl 9(S)-[1(S)-ethoxycarbonyl-3-phenylpropylamino]-octahydro-6,10-dioxo-6H-pyridazo[1,2-a][1,2]diazepine-1(S)-carboxylate were taken up in methanol and the solution was saturated with ammonia. The mixture was left to stand at 0° C. for 15 days and was then evaporated. Chromatography of the residue on silica gel using ethyl acetate/n-hexane (3:1) for the elution gave 340 mg of tert.butyl 9(S)-[1(S)-carbamoyl-3-phenylpropylamino]-octahydro-6,10-dioxo-6H-pyridazo[1,2-a][1,2]diazepine-1(S)-carboxylate in the form of a gum.

EXAMPLE 45

In a manner analogous to that described in Example 35, from 260 mg of tert.butyl 9(S)-[1(S)-carbamoyl-3-phenylpropylamino]-octahydro-6,10-dioxo-6H-pyridazo[1,2-a][1,2]diazepine-1(S)-carboxylate there were obtained 250 mg of 9(S)-[1(S)-carbamoyl-3-phenylpropylamino]-octahydro-6,10-dioxo-6H-pyridazo[1,2-a][1,2]diazepine-1(S)-carboxylic acid hydrobromide in the form of white crystals of melting point 170°–190° C. (decomposition) (from ethanol/ethyl acetate).

EXAMPLE 46

In a manner analogous to that described in Example 44, from 487 mg of tert.butyl 9(S)-[1(S)-ethoxycarbonyl-3-phenylpropylamino]-octahydro-6,10-dioxo-6H-pyridazo[1,2-a][1,2]diazepine-1(S)-carboxylate using ethanolic ethylamine there were obtained 260 mg of tert.butyl 9(S)-[1(S)-ethylcarbamoyl-3-phenylpropylamino]-octahydro-6,10-dioxo-6H-pyridazo[1,2-a][1,2]diazepine-1(S)-carboxylate in the form of a gum.

EXAMPLE 47

In a manner analogous to that described in Example 35, from 210 mg of tert.butyl 9(S)-[1(S)-ethylcarbamoyl-3-phenylpropylamino]-octahydro-6,10-dioxo-6H-pyridazo[1,2-a][1,2]diazepine-1(S)-carboxylate there were obtained 180 mg of 9(S)-[1(S)-ethylcarbamoyl-3-phenylpropylamino]-octahydro-6,10-dioxo-6H-pyridazo[1,2-a][1,2]diazepine-1(S)-carboxylic acid in the form of a white solid decomposing at above 170° C. after crystallization from ethanol/ethyl acetate.

EXAMPLE 48

In a manner analogous to that described in Example 1, from 241 mg of 9(S)-amino-octahydro-6,10-dioxo-6H-pyridazo[1,2-a][1,2]diazepine-1(S)-carboxylic acid and 576 mg of 2-oxo-5-phenylpentanoic acid there were obtained 100 mg of 9(S)-[1(R and S)-carboxy-4-phenylbutylamino]-octahydro-6,10-dioxo-6H-pyridazo[1,2-a][1,2]diazepine-1(S)-carboxylic acid in the form of a white solid.

EXAMPLE 49

In a manner analogous to that described in Example 1, from 241 mg of 9(S)-amino-octahydro-6,10-dioxo-6H-pyridazo[1,2-a][1,2]diazepine-1(S)-carboxylic acid and 612 mg of sodium phenylpyruvate monohydrate there were obtained 110 mg of 9(S)-[1(R and S)-carboxy-2-phenylethylamino]-octahydro-6,10-dioxo-6H-pyridazo[1,2-a][1,2]diazepine-1(S)-carboxylic acid in the form of a white solid.

EXAMPLE 50

In a manner analogous to that described in Example 1, from 241 mg of 9(S)-amino-octahydro-6,10-dioxo-6H-pyridazo[1,2-a][1,2]diazepine-1(S)-carboxylic acid and 432 mg of 2-oxo-5-methylhexanoic acid there were obtained 68 mg of 9(S)-[1(R and S)-carboxy-4-methylpentylamino]-octahydro-6,10-dioxo-6H-pyridazo[1,2-a][1,2]diazepine-1(S)-carboxylic acid in the form of a white solid.

EXAMPLE 51

In a manner analogous to that described in Example 31, from 2.97 g of tert.butyl 9(S)-amino-octahydro-6,10-dioxo-6H-pyridazo[1,2-a][1,2]diazepine-1(S)-carboxylate and 2.6 g of ethyl 2-bromo-5-methylhexanoate there were obtained 1.5 g (33%) of tert.butyl 9(S)-[1(R)-ethoxycarbonyl-4-methylpentylamino]-octahydro-6,10-dioxo-6H-pyridazo[1,2-a][1,2]diazepine-1(S)-carboxylate and 1.6 g (35%) of tert.butyl 9(S)-[1(S)-ethoxycarbonyl-4-methylpentylamino]-octahydro-6,10-dioxo-6H-pyridazo[1,2-a][1,2]-diazepine-1(S)-carboxylate, both in the form of pale yellow oils.

EXAMPLE 52

In a manner analogous to that described in Example 35, from 1.0 g of tert.butyl 9(S)-[1(R)-ethoxycarbonyl-4-methylpentylamino]-octahydro-6,10-dioxo-6H-pyridazo[1,2-a][1,2]diazepine-1(S)-carboxylate there was obtained 0.4 g (38%) of 9(S)-[1(R)-ethoxycarbonyl-4-methylpentylamino]-octahydro-6,10-dioxo-6H-pyridazo[1,2-a][1,2]diazepine-1(S)-carboxylic acid hydrobromide in the form of a white solid of melting point 220°–221° C. (from ethanol/ethyl acetate).

EXAMPLE 53

In a manner analogous to that described in Example 35, from 1 g of tert.butyl 9(S)-[1(S)-ethoxycarbonyl-4-methylpentylamino]-octahydro-6,10-dioxo-6H-pyridazo[1,2-a][1,2]diazepine-1(S)-carboxylate there was obtained 0.74 g (70%) of 9(S)-[1(S)-ethoxycarbonyl-4-methylpentylamino]-octahydro-6,10-dioxo-6H-pyridazo[1,2-a][1,2]diazepine-1(S)-carboxylic acid hydrobromide in the form of a white solid of melting point 209°-210° C. (from ethanol/ethyl acetate).

EXAMPLE 54

In a manner analogous to that described in Example 33, from 4.45 g of tert.butyl 9(S)-amino-octahydro-6,10-dioxo-6H-pyridazo[1,2-a][1,2]diazepine-1(S)-carboxylate and 7.21 g of ethyl 4-(4-chlorophenyl)-2-oxo-butanoate there were obtained 2.13 g (27%) of tert.butyl 9(S)-[3-(4-chlorophenyl)-1(R)-ethoxycarbonylpropylamino]-octahydro-6,10-dioxo-6H-pyridazo[1,2-a][1,2]diazepine-1(S)-carboxylate in the form of white crystals of melting point 82°-83° C. (from diethyl ether/n-hexane) and 1.49 g (19%) of tert.butyl 9(S)-[3-(4-chlorophenyl)-1(S)-ethoxycarbonylpropylamino]-octahydro-6,10-dioxo-6H-pyridazo[1,2-a][1,2]diazepine-1(S)-carboxylate in the form of white crystals of melting point 86°-88° C. (from diethyl ether/n-hexane).

EXAMPLE 55

In a manner analogous to that described in Example 35, from 1.28 g of tert.butyl 9(S)-[3-(4-chlorophenyl)-1(S)-ethoxycarbonylpropylamino]-octahydro-6,10-dioxo-6H-pyridazo[1,2-a][1,2]diazepine-1(S)-carboxylate there was obtained 0.78 g (57%) of 9(S)-[3-(4-chlorophenyl)-1(S)-ethoxycarbonylpropylamino]-octahydro-6,10-dioxo-6H-pyridazo[1,2-a][1,2]diazepine-1(S)-carboxylic acid in the form of white crystals of melting point 224°-225° C. (from ethanol/ethyl acetate).

EXAMPLE 56

In a manner analogous to that described in Example 33, from 4.45 g of tert.butyl 9(S)-amino-octahydro-6,10-dioxo-6H-pyridazo[1,2-a][1,2]diazepine-1(S)-carboxylate and 5.66 g of ethyl 4-(4-methoxyphenyl)-2-oxo-butanoate there were obtained 1.21 g (16%) of tert.butyl 9(S)-[1(R)-ethoxycarbonyl-3-(4-methoxphenyl)-propylamino]-octahydro-6,10-dioxo-6H-pyridazo[1,2-a][1,2]diazepine-1(S)-carboxylate in the form of white crystals of melting point 73°-74° C. (from diethyl ether/n-hexane) and 0.81 g (10%) of tert.butyl 9(S)-[1(S)-ethoxycarbonyl-3-(4-methoxyphenyl)-propylamino]-octahydro-6,10-dioxo-6H-pyridazo[1,2-a][1,2]diazepine-1(S)-carboxylate in the form of white needles of melting point 100°-101.5° C. (from diethyl ether/n-hexane).

EXAMPLE 57

In a manner analogous to that described in Example 35, from 0.71 g of tert.butyl 9(S)-[1(S)-ethoxycarbonyl-3-(4-methoxyphenyl)propylamino]-octahydro-6,10-dioxo-6H-pyridazo[1,2-a][1,2]-diazepine-1(S)-carboxylate there was obtained 0.49 g (66%) of 9(S)-[1(S)-ethoxycarbonyl-3-(4-methoxyphenyl)propylamino]-octahydro-6,10-dioxo-6H-pyridazo[1,2-a][1,2]diazepine-1(S)-carboxylic acid hydrobromide in the form of a white solid of melting point 123°-127° C. (from ethanol/ethyl acetate).

EXAMPLE 58

In a manner analogous to that described in Example 33, from 4.45 g of tert.butyl 9(S)-amino-octahydro-6,10-dioxo-6H-pyridazo[1,2-a][1,2]diazepine-1(S)-carboxylate and 8.46 g of ethyl 4-biphenylyl-2-oxo-butanoate there were obtained 1.83 g (22%) of tert.butyl 9(S)-[3-(4-biphenylyl)-1(R)-ethoxycarbonylpropylamino]-octahydro-6,10-dioxo-6H-pyridazo[1,2-a][1,2]diazepine-1(S)-carboxylate in the form of white crystals of melting point 136°-139° C. (from diethyl ether) and 1.56 g (18%) of tert.butyl 9(S)-[3-(4-biphenylyl)-1(S)-ethoxycarbonylpropylamino]-octahydro-6,10-dioxo-6H-pyridazo[1,2-a][1,2]diazepine-1(S)-carboxylate in the form of white crystals of melting point 101°-103° C. (from diethyl ether).

EXAMPLE 59

In a manner analogous to that described in Example 35, from 1.36 g of tert.butyl 9(S)-[3-(4-biphenylyl)-1(S)-ethoxycarbonylpropylamino]-octahydro-6,10-dioxo-6H-pyridazo[1,2-a][1,2]diazepine-1(S)-carboxylate there was obtained 0.63 g (45%) of 9(S)-[3-(4-biphenylyl)-1(S)-ethoxycarbonylpropylamino]-octahydro-6,10-dioxo-6H-pyridazo[1,2-a][1,2]diazepine-1(S)-carboxylic acid hydrobromide in the form of a hygroscopic white solid.

EXAMPLE 60

In a manner analogous to that described in Example 32, from 1.78 g of tert.butyl 9(S)-amino-octahydro-6,10-dioxo-6H-pyridazo[1,2-a][1,2]diazepine-1(S)-carboxylate and 2.62 g of ethyl 2(R,S)-trifluoromethanesulphonyloxy-6-phthalimidohexanoate there were obtained 1.62 g (46%) of tert.butyl 9(S)-[1(R)-ethoxycarbonyl-5-phthalimidopentylamino]-octahydro-6,10-dioxo-6H-pyridazo[1,2-a][1,2]diazepine-1(S)-carboxylate and 1.58 g (45%) of tert.butyl 9(S)-[1(S)-ethoxycarbonyl-5-phthalimidopentylamino]-octahydro-6,10-dioxo-6H-pyridazo[1,2-a][1,2]diazepine-1(S)-carboxylate, both in the form of pale yellow oils.

EXAMPLE 61

In a manner analogous to that described in Example 35, from 1.9 g of tert.butyl 9(S)-[1(R)-ethoxycarbonyl-5-phthalimidopentylamino]-octahydro-6,10-dioxo-6H-pyridazo[1,2-a][1,2]diazepine-1(S)-carboxylate there were obtained 1.36 g (69%) of 9(S)-[1(R)-ethoxycarbonyl-5-phthalimidopentylamino]-octahydro-6,10-dioxo-6H-pyridazo[1,2-a][1,2]diazepine-1(S)-carboxylic acid hydrobromide in the form of a white solid of melting point 207°-208° C. (from ethanol/ethyl acetate).

EXAMPLE 62

In a manner analogous to that described in Example 35, from 1.79 g of tert.butyl 9(S)-[1(S)-ethoxycarbonyl-5-phthalimidopentylamino]-octahydro-6,10-dioxo-6H-pyridazo[1,2-a][1,2]diazepine-1(S)-carboxylate there were obtained 1.36 l g (74%) of 9(S)-[1(S)-ethoxycarbonyl-5-phthalimidopentylamino]-octahydro-6,10-dioxo-6H-pyridazo[1,2-a][1,2]diazepine-1(S)-carboxylic acid hydrobromide in the form of a white solid of melting point 227°-229° C. (from ethanol/ethyl acetate).

EXAMPLE 63

A solution of 1.15 g of tert.butyl 8(S)-amino-2,3,6,7,8,9-hexahydro-5,9-dioxo-1H,5H-pyrazolo[1,2-a][1,2]diazepine-1(S)-carboxylate and 3.10 g of ethyl 2-oxo-4-phenylbutanoate in 50 ml of ethanol was hydrogenated over 1.0 g of 10% palladium-on-carbon in the presence of molecular sieve at 4 atmospheres for 48 hours. The catalyst was removed by filtration and the filtrate was evaporated. The residue was chromatographed on silica gel to give 0.18 g of tert.butyl 8(S)-[1(R)-ethoxycarbonyl-3-phenylpropylamino]-2,3,6,7,8,9-hexahydro-5,9-dioxo-1H,5H-pyrazolo[1,2-a][1,2]diazepine-1(S)-carboxylate in the form of a pale yellow oil and subsequently 0.19 g of tert.butyl 8(S)-[1(S)-ethoxycarbonyl-3-phenylpropylamino]-2,3,6,7,8,9-hexahydro-5,9-dioxo-1H,5H-pyrazolo[1,2-a][1,2]diazepine-1(S)-carboxylate in the form of a pale yellow oil.

The tert.butyl 8(S)-amino-2,3,6,7,8,9-hexahydro-5,9-dioxo-1H,5H-pyrazolo[1,2-a][1,2]diazepine-1(S)-carboxylate used as the starting material was prepared as follows:

2.48 g of tert.butyl 2,3,6,7,8,9-hexahydro-5,9-dioxo-8(S)-phthalimido-1H,5H-pyrazolo[1,2-a][1,2]diazepine-1(S)-carboxylate [prepared as described in Example 3(D)] were stirred at room temperature for 0.5 hours in 80 ml of ethanol with 0.3 g of hydrazine hydrate and the mixture was then evaporated. 90 ml of 2N acetic acid were added, the mixture was stirred at room temperature for 1 hour and was then filtered. The filtrate was made basic with solid sodium carbonate and then extracted twice with dichloromethane. The combined dichloromethane extracts were dried over magnesium sulphate and evaporated to give 1.58 g (93%) of tert.butyl 8(S)-amino-2,3,6,7,8,9-hexahydro-5,9-dioxo-1H,5H-pyrazolo[1,2-a][1,2]diazepine-1(S)-carboxylate in the form of a gum.

EXAMPLE 64

A solution of 0.15 g of tert.butyl 8(S)-[1(S)-ethoxycarbonyl-3-phenylpropylamino]-2,3,6,7,8,9-hexahydro-5,9-dioxo-1H,5H-pyrazolo[1,2-a][1,2]diazepine-1(S)-carboxylate in 0.3 ml of acetic acid was treated at room temperature for 0.5 hour with 1.3 ml of 45% hydrogen bromide solution in acetic acid. The mixture was then evaporated and the resulting oily solid was triturated with diethyl ether to give 0.11 g (65%) of 8(S)-[1(S)-ethoxycarbonyl-3-phenylpropylamino]-2,3,6,7,8,9-hexahydro-5,9-dioxo-1H,5H-pyrazolo[1,2-a][1,2]diazepine-1(S)-carboxylic acid hydrobromide in the form of a light tan coloured solid of melting point 207°–210° C.

EXAMPLE 65

1.27 g of benzyl 9(S)-amino-octahydro-10-oxo-6H-pyridazo[1,2-a][1,2]diazepine-1(S)-carboxylate, 1.36 g of ethyl 2(R)-trifluoromethanesulphonyloxy-4-phenylbutanoate and 0.4 g of triethylamine in 10 ml of acetonitrile were stirred at room temperature for 16 hours. The solvent was removed by evaporation and the residue was partitioned between water and ethyl acetate. The organic solution was dried over magnesium sulphate and evaporated. After purification by chromatography on silica gel using ethyl acetate/n-hexane (1:1) for the elution there were obtained 1.55 g of benzyl 9(S)-[1(S)-ethoxycarbonyl-3-phenylpropylamino]-octahydro-10-oxo-6H-pyridazo[1,2-a][1,2]diazepine-1(S)-carboxylate in the form of a colourless oil.

The benzyl 9(S)-amino-octahydro-10-oxo-6H-pyridazo[1,2-a][1,2]diazepine-1(S)-carboxylate used as the starting material was prepared as follows:

(A) 2 g of α(S)-(3-bromopropyl)-1,3-dioxo-2-isoindolineacetic acid in 15 ml of dry diethyl ether were stirred with 1.34 g of phosphorus pentachloride at room temperature for 1.5 hours. The solvent was removed by evaporation and the residue was re-evaporated twice with toluene and then dissolved in 25 ml of dichloromethane. The solution was stirred while 1.64 g of tert.butyl 1-benzyloxycarbonyl-hexahydro-3-pyridazinecarboxylate in 10 ml of dichloromethane were added, followed by 25 ml of saturated aqueous sodium bicarbonate solution. The mixture was stirred at room temperature for 3 hours and the layers were then separated. The organic phase was washed with sodium chloride solution, dried over magnesium sulphate and evaporated. After purification by chromatography on silica gel using toluene/acetonitrile (4:1) for the elution, there were obtained 2.4 g (75%) of 1-benzyl 3-tert.butyl 2-(5-bromo-2-phthalimidovaleryl)-1,3-pyridazinedicarboxylate (2 diastereomers) in the form of an oil.

(B) 2.37 g of 1-benzyl 3-tert.butyl 2-(5-bromo-2-phthalimidovaleryl)-1,3-pyridazinedicarboxylate (2 diastereomers) were dissolved in 25 ml of ethanol and the solution was hydrogenated at atmospheric pressure over 50 mg of 10% palladium-on-carbon until the uptake of hydrogen had ceased. The catalyst was removed by filtration and the filtrate was evaporated to give 1.79 g (96%) of tert.butyl 2-(5-bromo-2-phthalimidovaleryl)-3-pyridazinecarboxylate (2 diastereomers) in the form of an oil.

(C) 15 g of tert.butyl 2-(5-bromo-2-phthalimidovaleryl)-3-pyridazinecarboxylate (2 diastereomers) were dissolved in 200 ml of dry dimethylformamide and the solution was stirred at 80° C. for 60 hours. The solvent was removed by evaporation and the residue was partitioned between water and dichloromethane. The organic solution was dried over magnesium sulphate and evaporated. After purification of the residue by chromatography on silica gel using toluene/acetic acid (4:1) for the elution, there were obtained 3.6 g (33%) of octahydro-10-oxo-9(S)-phthalimido-6H-pyridazo[1,2-a][1,2]diazepine-1(S)-carboxylic acid in the form of white crystals of melting point 256°–258° C. (from ethyl acetate/n-hexane) and 1.4 g (13%) of octahydro-10-oxo-9(S)-phthalimido-6H-pyridazo[1,2-a][1,2]diazepine-1(R)-carboxylic acid in the form of white crystals of melting point 241°–244° C. (from ethyl acetate/n-hexane).

(D) 3.57 g of octahydro-10-oxo-9(S)-phthalimido-6H-pyridazo[1,2-a][1,2]diazepine-1(S)-carboxylic acid were dissolved in 25 ml of 0.4M ethanolic sodium hydroxide solution and 0.5 g of hydrazine hydrate in 25 ml of ethanol was added. The mixture was stirred at room temperature for 4 hours and then evaporated. 80 ml of 2N acetic acid were added, the mixture was stirred at room temperature for 3 hours and then filtered. The filtrate was evaporated and the residue was applied to a column of 40 g of Duolite C225 ion exchange resin (H+form). The column was eluted with water containing 2% pyridine and the eluate was evaporated to give 1.7 g (75%) of 9(S)-amino-octahydro-10-oxo-6H-pyridazo[1,2-a][1,2]diazepine-1(S)-carboxylic acid in the form of a white solid. After crystallization from water/acetonitrile, this acid melted at 247°–249° C. (decomposition); $[α]_D^{20} = -121.9°$ (c=0.675 in water).

(E) 1.6 g of 9(S)-amino-octahydro-10-oxo-8H-pyridazo[1,2-a][1,2]diazepine-1(S)-carboxylic acid in 5 ml of methanol were treated with a solution of phenyldiazomethane in diethyl ether until starting material no longer remained. The solvents were removed by evaporation and the residue was partitioned between dichloromethane and 2N hydrochloric acid. The aqueous solution was made basic using potassium carbonate and extracted with dichloromethane. The organic solution was washed with sodium chloride solution, dried over magnesium sulphate and evaporated to give 1.36 g of crude benzyl 9(S)-amino-octahydro-10-oxo-6H-pyridazo[1,2-a][1,2]diazepine-1(S)-carboxylate in the form of an oil which was used without further purification.

EXAMPLE 66

1.35 g of benzyl 9(S)-[1(S)-ethoxycarbonyl-3-phenylpropylamino]-octahydro-10-oxo-6H-pyridazo[1,2-a][1,2]diazepine-1(S)-carboxylate were dissolved in 20 ml of ethanol and the solution was hydrogenated at atmospheric pressure over 50 mg of 10% palladium-on-carbon until the uptake of hydrogen had ceased. The catalyst was removed by filtration and the filtrate was evaporated to give 1.02 g of 9(S)-[1(S)-ethoxycarbonyl-3-phenylpropylamino]-octahydro-10-oxo-6H-pyridazo[1,2-a][1,2]diazepine-1(S)-carboxylic acid in the form of a colourless oil. This oil was dissolved in 10 ml of ethyl acetate and 2 ml of 2.5N hydrogen chloride in ethyl acetate were added. 100 ml of diethyl ether were then added and the mixture was stirred for 1 hour. The resulting solid was filtered off, there being obtained 0.72 g (60%) of 9(S)-[1(S)-ethoxycarbonyl-3-phenylpropylamino]-octahydro-10-oxo-6H-pyridazo[1,2-a][1,2]-diazepine-1(S)-carboxylic acid hydrochloride in the form of a hygroscopic solid; $[\alpha]_D^{20} = -69.1°$ (c=1 in water).

EXAMPLE 67

In a manner analogous to that described in Example 31, from 1.10 g of tert.butyl 9(S)-amino-octahydro-6,10-dioxo-6H-pyridazo[1,2-a][1,2]diazepine-1(S)-carboxylate, 1.40 g of ethyl 2-bromo-6-benzyloxyformamidohexanoate and 0.37 g of triethylamine there was obtained 0.4 g of tert.butyl 9(S)[-5-benzyloxyformamido-1(R)-ethoxycarbonylpentylamino]-octahydro-6,10-dioxo-6H-pyridazo[1,2-a][1,2]diazepine-1(S)-carboxylate in the form of a pale yellow oil and 0.33 g of tert.butyl 9(S)-[5-benzyloxyformamido-1(S)-ethoxycarbonylpentylamino]-octahydro-6,10-dioxo-6H-pyridazo[1,2-a][1,2]diazepine-1(S)-carboxylate in the form of a pale yellow oil.

EXAMPLE 68

By treating tert.butyl 9(S)-[5-benzyloxyformamido-1(S)-ethoxycarbonylpentylamino]-octahydro-6,10-dioxo-6H-pyridazo[1,2-a][1,2]diazepine-1(S)-carboxylate with trifluoroacetic acid there can be obtained 9(S)-[5-benzyloxyformamido-1(S)-ethoxycarbonylpentylamino]-octahydro-6,10-dioxo-6H-pyridazo[1,2-a][1,2]diazepine-1(S)-carboxylic acid.

The following Examples illustrate pharmaceutical preparations containing the compounds provided by this invention:

EXAMPLE A

Tablets containing the following ingredients can be produced in a conventional manner:

| Ingredient | Per tablet |
| --- | --- |
| Compound of formula I | 10.0 mg |
| Lactose | 125.0 mg |
| Maize starch | 75.0 mg |
| Talc | 4.0 mg |
| Magnesium stearate | 1.0 mg |
| Total weight | 215.0 mg |

EXAMPLE B

Capsules containing the following ingredients are produced in a conventional manner:

| Ingredient | Per tablet |
| --- | --- |
| Compound of formula I | 25.0 mg |
| Lactose | 150.0 mg |
| Maize starch | 20.0 mg |
| Talc | 5.0 mg |
| Total capsule content | 200.0 mg |

We claim:
1. Compounds of the formula

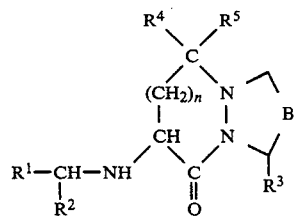

wherein B represents an ethylene group, $R^1$ represents a hydrogen atom or an alkyl, aralkyl, amino-alkyl, monoalkylamino-alkyl, dialkylamino-alkyl, acylamino-alkyl, phthalimido-alkyl, alkoxycarbonylamino-alkyl, aryloxycarbonylamino-alkyl, aralkoxycarbonylamino-alkyl, alkylaminocarbonylamino-alkyl, arylaminocarbonyl-aminoalkyl, aralkylaminocarbonylamino-alkyl, alkylsulphonylamino-alkyl or arylsulphonylamino-alkyl group, $R^2$ represents a carboxyl, alkoxycarbonyl or aralkoxycarbonyl group or a group of the formula

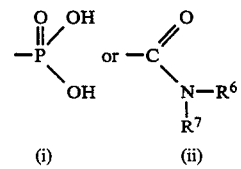

$R^3$ represents a carboxyl, alkoxy-carbonyl or aralkoxycarbonyl group, $R^4$ and $R^5$ each represent a hydrogen atom or $R^4$ and $R^5$ together represent an oxo group, $R^6$ and $R^7$ each represent a hydrogen atom or an alkyl or aralkyl group or $R^6$ and $R^7$ together with the nitrogen atom to which they are attached represent a 5-membered or 6-membered heteromonocyclic ring which may contain a further nitrogen atom or an oxygen or sulphur atom, and n is 2, and pharmaceutically acceptable salts thereof.

2. Compounds as claimed in claim 1, wherein $R^1$ represents a hydrogen atom or an alkyl, aralkyl, amino-alkyl, monoalkylamino-alkyl, dialkylamino-alkyl, acylamino-alkyl, alkoxycarbonylamino-alkyl, aryloxycarbonylamino-alkyl, aralkoxycarbonylamino-alkyl, alkylaminocarbonylamino-alkyl, arylaminocarbonylamino-alkyl, aralkylaminocarbonylamino-alkyl, alkylsulphonylamino-alkyl or arylsulphonylamino-alkyl, $R^2$ represents a carboxyl or alkoxycarbonyl group or a group of formula (i) and $R^3$ represents a carboxyl or alkoxycarbonyl group.

3. Compounds as claimed in claim 1 wherein $R^1$ represents an alkyl, aralkyl, acylamino-alkyl, phthalimido-alkyl, aralkoxycarbonylamino-alkyl or arylaminocarbonylamino-alkyl group.

4. Compounds as claimed in claim 1 wherein $R^2$ represents a carboxyl, alkoxycarbonyl or aralkoxycarbonyl group or a group of formula (ii).

5. Compounds as claimed in claim 1 wherein $R^3$ represents a carboxyl group.

6. Compounds as claimed in claim 1 wherein B represents an ethylene group, $R^1$ represents an alkyl, aralkyl, acylaminoalkyl, phthalimido-alkyl, aralkoxycarbonylamino-alkyl or arylaminocarbonylamino-alkyl group, $R^2$ represents a carboxyl, alkoxycarbonyl or aralkoxycarbonyl group or a group of formula (ii), and $R^3$ represents a carboxyl group.

7. In accordance with claim 1, the compound, 9-(1-Carboxy-3-phenylpropylamino)-octahydro-6,10-dioxo-6H-pyridazo[1,2-a][1,2]diazepine-1-carboxylic acid.

8. In accordance with claim 1, the compound, 9-(1-Ethoxycarbonyl-3-phenylpropylamino)-octahydro-6,10-dioxo-6H-pyridazo[1,2-a][1,2]diazepine-1-carboxylic acid.

9. In accordance with claim 1, the compound, 9-(1-Benzyloxycarbonyl-3-phenylpropylamino)-octahydro-6,10-dioxo-6H-pyridazo[1,2-a][1,2]diazepine-1-carboxylic acid.

10. In accordance with claim 1, the compound, 9-(1-Carbamoyl-3-phenylpropylamino)-octahydro-6,10-dioxo-6H-pyridazo[1,2-a][1,2]diazepine-1-carboxylic acid.

11. In accordance with claim 1, the compound, 9-(1-Ethylcarbamoyl-3-phenylpropylamino)-octahydro-6,10-dioxo-6H-pyridazo[1,2-a][1,2]diazepine-1-carboxylic acid.

12. In accordance with claim 1, the compound, 9-(1-Carboxy-4-phenylbutylamino)-octahydro-6,10-dioxo-6H-pyridazo[1,2-a][1,2]diazepine-1-carboxylic acid.

13. In accordance with claim 1, the compound, 9-(1-Carboxy-2-phenylethylamino)-octahydro-6,10-dioxo-6H-pyridazo[1,2-a][1,2]diazepine-1-carboxylic acid.

14. In accordance with claim 1, the compound, 9-(1-Carboxy-4-methylpentylamino)-octahydro-6,10-dioxo-6H-pyridazo[1,2-a][1,2]diazepine-1-carboxylic acid.

15. In accordance with claim 1, the compound, 9-(1-Ethoxycarbonyl-4-methylpentylamino)-octahydro-6,10-dioxo-6H-pyridazo[1,2-a][1,2]diazepine-1-carboxylic acid.

16. In accordance with claim 1, the compound, 9-[3-(4-Chlorophenyl)-1-ethoxycarbonylpropylamino]-octahydro-6,10-dioxo-6H-pyridazo[1,2-a][1,2]diazepine-1-carboxylic acid.

17. In accordance with claim 1, the compound, 9-[1-Ethoxycarbonyl-3-(4-methoxyphenyl)propylamino]-octahydro-6,10-dioxo-6H-pyridazo[1,2-a][1,2]diazepine-1-carboxylic acid.

18. In accordance with claim 1, the compound, 9-[3-(4-Biphenylyl)-1-ethoxycarbonylpropylamino]-octahydro-6,10-dioxo-6H-pyridazo[1,2-a][1,2]diazepine-1-carboxylic acid.

19. In accordance with claim 1, the compound, 9-(1-Ethoxycarbonyl-5-phthalimidopentylamino)-octahydro-6,10-dioxo-6H-pyridazo[1,2-a][1,2]diazepine-1-carboxylic acid.

20. In accordance with claim 1, the compound, 9-(1-Ethoxycarbonyl-3-phenylpropylamino)-octahydro-10-oxo-6H-pyridazo[1,2-a][1,2]diazepine-1-carboxylic acid.

21. In accordance with claim 1, the compound, 9-(5-Benzyloxyformamido-1-ethoxycarbonylpentylamino)-octahydro-6,10-dioxo-6H-pyridazo[1,2-a][1,2]diazepine-1-carboxylic acid.

22. A compound selected from the following:
Tert.butyl 9-(1-ethoxycarbonyl-3-phenylpropylamino)-octahydro-6,10-dioxo-6H-pyridazo[1,2-a][1,2]diazepine-1-carboxylate,
tert.butyl 9-(1-benzyloxycarbonyl-3-phenylpropylamino)-octahydro-6,10-dioxo-6H-pyridazo[1,2-a][1,2]diazepine-1-carboxylate,
methyl 9-(1-benzyloxycarbonyl-3-phenylpropylamino)-octahydro-6,10-dioxo-6H-pyridazo[1,2-a][1,2]diazepine-1-carboxylate,
methyl-9-(1-carboxy-3-phenylpropylamino)-octahydro-6,10-dioxo-6H-pyridazo[1,2-a][1,2]diazepine-1-carboxylate,
methyl 9-(1-ethoxycarbonyl-3-phenylpropylamino)-octahydro-6,10-dioxo-6H-pyridazo[1,2-a][1,2]diazepine-1-carboxylate,
ethyl 9-(1-ethoxycarbonyl-3-phenylpropylamino)-octahydro-6,10-dioxo-6H-pyridazo[1,2-a][1,2]diazepine-1-carboxylate,
tert.butyl 9-(1-carbamoyl-3-phenylpropylamino)-octahydro-6,10-dioxo-6H-pyridazo[1,2-a][1,2]diazepine-1-carboxylate,
tert.butyl 9-(1-ethylcarbamoyl-3-phenylpropylamino)-octahydro-6,10-dioxo-6H-pyridazo[1,2-a][1,2]diazepine-1-carboxylate,
tert.butyl 9-(1-ethoxycarbonyl-4-methylpentylamino)-octahydro-6,10-dioxo-6H-pyridazo[1,2-a][1,2]diazepine-1-carboxylate,
tert.butyl 9-[3-(4-chlorophenyl)-1-ethoxycarbonylpropylamino]-octahydro-6,10-dioxo-6H-pyridazo[1,2-a][1,2]diazepine-1-carboxylate,
tert.butyl 9-[1-ethoxycarbonyl-3-(4-methoxyphenyl)propylamino]-octahydro-6,10-dioxo-6H-pyridazo[1,2-a][1,2]diazepine-1-carboxylate,
tert.butyl 9-[3-(4-biphenylyl)-1-ethoxycarbonylpropylamino]-octahydro-6,10-dioxo-6H-pyridazo[1,2-a][1,2]diazepine-1-carboxylate,
tert.butyl 9-(1-ethoxycarbonyl-5-phthalimidopentylamino)-octahydro-6,10-dioxo-6H-pyridazo[1,2-a][1,2]diazepine-1-carboxylate,
benzyl 9-(1-ethoxycarbonyl-3-phenylpropylamino)-octahydro-10-oxo-6H-pyridazo[1,2-a][1,2]diazepine-1-carboxylate and
tert.butyl 9-(5-benzyloxyformamido-1-ethoxycarbonylpentylamino)-octahydro-6,10-dioxo-6H-pyridazo[1,2-a][1,2]diazepine-1-carboxylate.

23. A compound as set forth in claim 1 wherein the configuration at each asymmetric carbon atom is (S).

24. A compound as set forth in claim 22 wherein the configuration at each asymmetric carbon atom is (S).

25. A compound of the formula

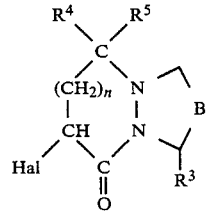

II wherein B represents an ethylene group, $R^3$ represents a carboxyl, alkoxycarbonyl or aralkoxycarbonyl group, $R^4$ and $R^5$ each represent a hydrogen atom or $R^4$ and $R^5$ together represent an oxo group, Hal represents a halogen atom and n is 2.

26. A compound of the formula

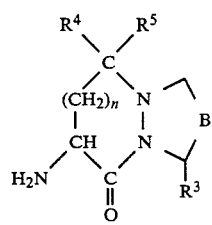
IV wherein B represents an ethylene group, $R^3$ represents a carboxyl, alkoxycarbonyl or aralkoxycarbonyl group, $R^4$ and $R^5$ each represent a hydrogen atom or $R^4$ and $R^5$ together represent and oxo group and n is 2.

27. An azide of the formula

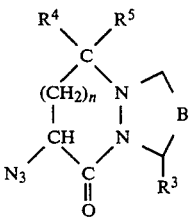
XV wherein B represents an ethylene group, $R^3$ represents a carboxyl, alkoxycarbonyl or aralkoxycarbonyl group, $R^4$ and $R^5$ each represent a hydrogen atom or $R^4$ and $R^5$ together represent an oxo group and n is 2.

28. A compound of the formula

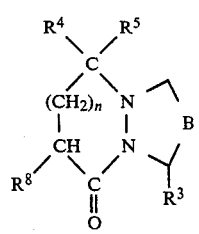
XVIIa wherein B represents an ethylene group, $R^3$ represents a carboxyl, alkoxycarbonyl or aralkoxycarbonyl group, $R^4$ and $R^5$ each represent a hydrogen atom or $R^4$ and $R^5$ together represent an oxo group, $R^8$ represents a phthaloylamino group and n is 2.

* * * * *